(12) United States Patent
Sabiev et al.

(10) Patent No.: US 11,331,478 B2
(45) Date of Patent: May 17, 2022

(54) WIRELESS IONTOPHORESIS PATCH AND CONTROLLER

(71) Applicant: United States Government as Represented by the Department of Veterans Affairs, Washington, DC (US)

(72) Inventors: Anton Sabiev, Forest Hills, NY (US); William Bauman, New Rochelle, NY (US); Mark Korsten, Hastings-on-Hudson, NY (US)

(73) Assignee: United States Government as Represented by the Department of Veterans Affairs, Washington, DC (US)

( * ) Notice: Subject to any disclaimer, the term of this patent is extended or adjusted under 35 U.S.C. 154(b) by 235 days.

(21) Appl. No.: 16/442,082

(22) Filed: Jun. 14, 2019

(65) Prior Publication Data
US 2019/0381311 A1 Dec. 19, 2019

Related U.S. Application Data

(60) Provisional application No. 62/685,162, filed on Jun. 14, 2018.

(51) Int. Cl.
*A61N 1/30* (2006.01)

(52) U.S. Cl.
CPC ..................... *A61N 1/30* (2013.01)

(58) Field of Classification Search
CPC ....... A61N 1/0448; A61N 1/30; A61N 1/0492
See application file for complete search history.

(56) References Cited

U.S. PATENT DOCUMENTS 6,006,130 A * 12/1999 Higo ................... A61N 1/0436
604/20
6,421,561 B1 7/2002 Morris
(Continued)

FOREIGN PATENT DOCUMENTS

WO WO 2017/0139794 A2 8/2017

OTHER PUBLICATIONS

International Search Report and Written Opinion were dated Aug. 22, 2019 by the International Searching Authority for International Application No. PCT/US2019/037321, filed on Jun. 14, 2019 (Applicant—Anton Sabiev) (11 Pages).
(Continued)

*Primary Examiner* — Deanna K Hall
(74) *Attorney, Agent, or Firm* — Ballard Spahr LLP

(57) ABSTRACT

An iontophoresis system for positioning against skin of a subject is disclosed. The iontophoresis system can comprise at least one vessel having a solvent therein. An anode apparatus can couple to the at least one vessel. The anode apparatus can comprise a first reservoir configured to receive the solvent from the at least one vessel so that, when received into the first reservoir, the solvent makes contact with the skin of the subject, and a first electrode positioned above the first reservoir. A cathode apparatus can couple to the at least one vessel. The cathode apparatus can comprise a second reservoir configured to receive the solvent from the at least one vessel so that, when received into the first reservoir, the solvent makes contact with the skin of the subject, and a second electrode positioned above the second reservoir.

22 Claims, 15 Drawing Sheets

(56) References Cited

U.S. PATENT DOCUMENTS

| | | |
|---|---|---|
| 6,653,014 B2 | 11/2003 | Anderson et al. |
| 7,016,723 B2 | 3/2006 | Morris |
| 7,031,768 B2 | 4/2006 | Anderson et al. |
| 7,031,769 B2 | 4/2006 | Anderson et al. |
| 7,635,709 B2 | 12/2009 | Korsten |
| 8,239,018 B2 | 8/2012 | Anderson et al. |
| 9,492,650 B2 | 11/2016 | Krinke |
| 2005/0004506 A1 | 1/2005 | Gyory |
| 2007/0093789 A1* | 4/2007 | Smith .................... A61P 17/02 604/890.1 |
| 2012/0041338 A1* | 2/2012 | Chickering, III .. A61B 5/14514 600/575 |
| 2016/0206512 A1 | 7/2016 | Chhikara et al. |
| 2017/0100572 A1 | 4/2017 | Zumbrunn et al. |
| 2017/0151330 A1 | 6/2017 | Harris et al. |

OTHER PUBLICATIONS

U.S. Appl. No. 62/685,162, filed Jun. 14, 2018, Anton Sabiev.
PCT, PCT/US2019/037321, Jun. 14, 2019, Anton Sabiev.
Korsten, M. A., Lyons, B. L., Radulovic, M., Cummings, T. M., Sikka, G., Singh, K., . . . & Bauman, W. A. (2018). Delivery of neostigmine and glycopyrrolate by iontophoresis: a nonrandomized study in individuals with spinal cord injury. Spinal cord, 56(3), 212-217.

* cited by examiner

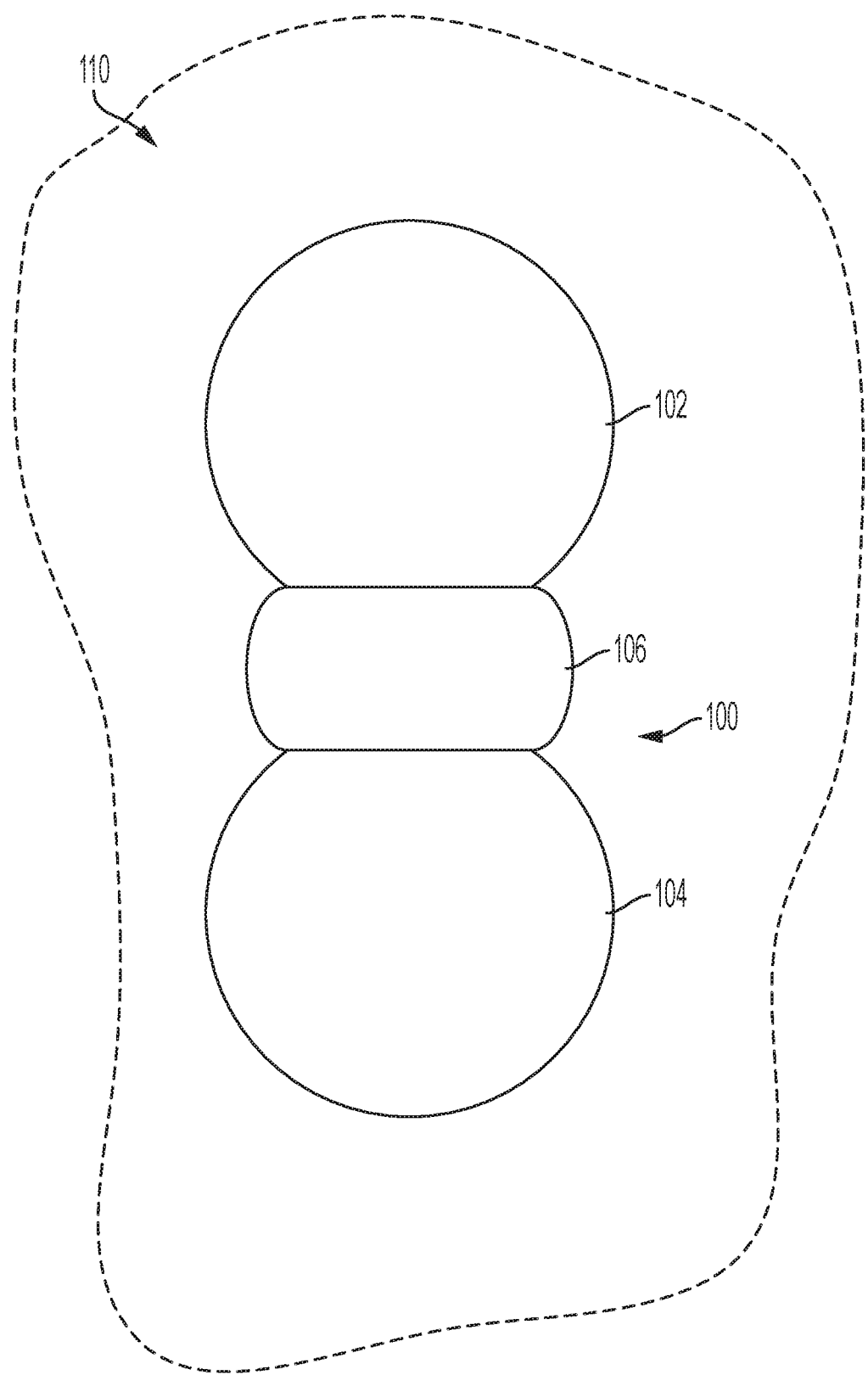
FIG. 1A (TOP VIEW)

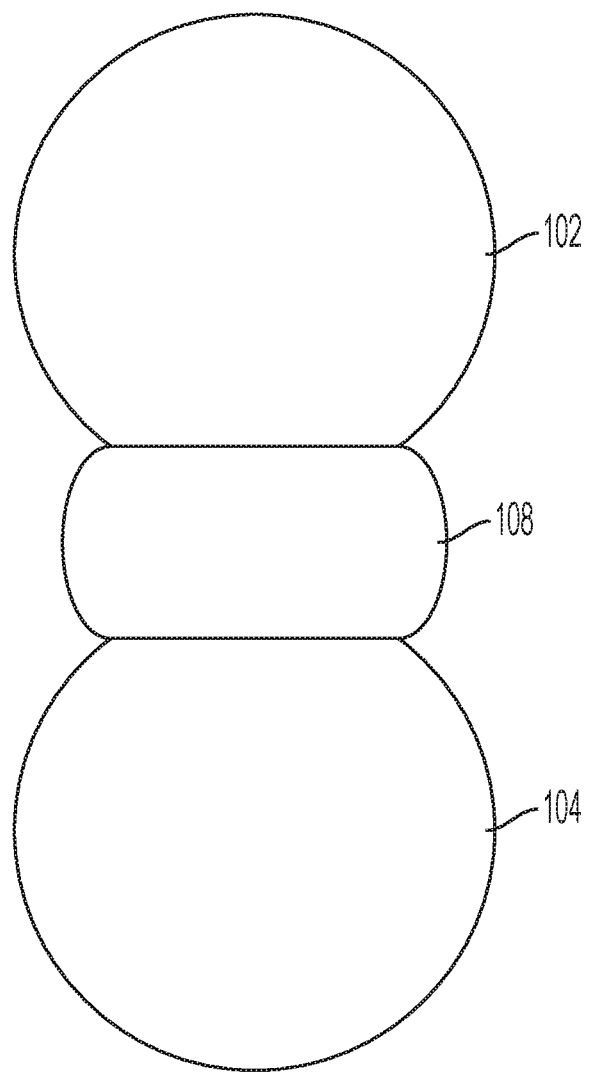
FIG. 1B (BOTTOM VIEW)

WIRELESS IONTOPHORESIS PATCH AND CONTROLLER

CROSS-REFERENCE TO RELATED APPLICATION

This application claims priority to and the benefit of the filing date of U.S. Provisional Patent Application No. 62/685,162, filed Jun. 14, 2018, the contents of which are incorporated herein by reference in their entirety.

FIELD

The present invention generally relates to iontophoresis and more particularly relates to a wireless iontophoresis patch and controller.

BACKGROUND

Iontophoresis is a process that utilizes direct electrical current to drive ionized chemical agents through the intact skin. For example, many drugs when dissolved in liquid dissociate into positively and negatively charged ions and, hence, become suitable for delivery through the skin by iontophoresis. Accordingly, the ions with a positive or negative electrical charge can be driven through the skin by the repelling action of an active electrode. A positive and/or a negative electrode connected to a respective electrical source can act as an active electrode for delivering charged ions of substances. Thus, when delivering a positively-charged drug through the skin of a subject by iontophoresis, the electrode contacting the solution containing the drug must be connected to the positive pole of the electrical source, and the ground electrode which contacts the skin of the subject is connected to the negative pole of the electrical source to provide a return path for the direct electric current.

Although iontophoresis successfully delivers drugs through the intact skin, conventional products and methods for delivery of drugs through the skin using iontophoresis may be associated with several adverse outcomes. One particular challenge with using iontophoresis for drug delivery is that the skin's physical reaction to the electrical stimulation of iontophoresis electrode is to polarize the skin with the like-charge to the direct electric current, and polarized skin decreases the effectiveness of the delivery of agents by iontophoresis for any given voltage. The conventional solution to polarization of the skin is to increase the voltage of the electrical stimulation. However, the increased voltage during iontophoresis may cause injury to the skin of the subject. In some cases, localized injuries to the skin of the subject allow a disproportionate amount of the electric current to enter a small fraction of the total available skin surface under an electrode, causing thermal injury to the skin. Conventional iontophoresis products and methods have so severely damaged the skin of patients that the products were ultimately blocked from being commercially available to consumers by the Food and Drug Administration ("FDA").

Further, conventional iontophoresis systems use gels. Such gels have a relatively short shelf life. Moreover, said gels can commonly trap sheets of air bubbles on the surface of the skin, reducing the effective contact area of the gel with the patient's skin surface, which can result in burns. Accordingly, an improved system is desirable.

SUMMARY

Described herein, in various aspects, is an iontophoresis system for positioning against skin of a subject. The iontophoresis system can comprise at least one vessel having a solvent therein, an anode apparatus comprising a first reservoir configured to receive the solvent from the at least one vessel so that, when received into the first reservoir, the solvent makes contact with the skin of the subject, a first electrode positioned above the first reservoir, and a cathode apparatus comprising a second reservoir configured to receive the solvent from the at least one vessel so that, when received into the first reservoir, the solvent makes contact with the skin of the subject; a second electrode positioned above the second reservoir.

The iontophoresis system can further comprise a first negative pressure source configured to remove air from the first reservoir.

The iontophoresis system can further comprise a one-way valve positioned in fluid communication with the first negative pressure source and ambient air, wherein the first negative pressure source comprises a resilient compressible chamber.

The first negative pressure source can comprise a volume having a negative pressure trapped therein. The iontophoresis system can further comprises a needle configured to pierce the volume having a negative pressure trapped therein, and a conduit that provides fluid communication between the needle and the first reservoir.

The first negative pressure source can comprises a syringe chamber, a plunger movable within the syringe chamber, and a check valve configured to allow fluid into the syringe chamber and inhibit fluid from exiting the syringe chamber.

The iontophoresis system can further comprise a chamber having a powdered agent disposed therein, wherein the chamber is positioned between, and configured to be in fluid communication with, the first reservoir and the at least one vessel.

The iontophoresis system can further comprise a powdered agent disposed in the first reservoir.

The at least one vessel can comprises a first vessel that is configured to deliver solvent to the first reservoir and a second vessel that is configured to deliver solvent to the second reservoir.

The iontophoresis system can further comprise a depolarizer electrode positioned below the first reservoir and positioned to make contact with the skin of the subject.

The iontophoresis system can further comprise a controller device comprising: a non-transitory computer readable medium configured to store executable programmed modules; and a processor communicatively coupled with the non-transitory computer readable medium and configured to execute programmed modules stored therein, wherein the controller is configured to control the first electrode to periodically generate a therapeutic electrical pulse having a first charge that creates an electrical voltage difference between the first electrode and the second electrode to transport the charged therapeutic agent through the skin of the subject.

The iontophoresis system can further comprise a depolarizer electrode positioned below the first reservoir and positioned to make contact with the skin of the subject, wherein the controller is configured to control the depolarizer electrode to periodically generate a depolarizing electrical pulse having a second charge opposite the first charge that creates an electrical voltage difference between the depolarizer electrode and the surface of the skin to depolarize the skin of the subject.

The iontophoresis system can further comprise an insulator bridge configured to provide electrical and physical insulation between the first electrode and the second electrode.

The at least one vessel can comprise a first fluid connector, and the anode apparatus comprises a second fluid connector that is configured to mate with the first fluid connector, wherein the second fluid connector comprises a seal.

The powdered agent can comprise an ionic surfactant that facilitates the passage of the powdered agent transdermally.

The powdered agent comprise citric acid.

The powdered agent can comprise a di-protic or tri-protic acid.

The powdered agent can comprise a quantity of acid that, when mixed with the solvent to fill the anode reservoir, provides a concentration of the acid that is non-irritating to the skin.

The concentration can range from 0.2% to 2%.

An acid solution resulting from mixing the powdered agent and solvent can provide buffering to the electrochemical generation of a base.

The base can be hydroxide ions.

A method for iontophoresis can comprise: securing an anode apparatus to the skin of the subject, the anode apparatus having a first reservoir configured to receive solvent so that, when received into the first reservoir, the solvent makes contact with the skin of the subject, and a first electrode positioned above the first reservoir; securing a cathode apparatus to the skin of the subject, the cathode apparatus having a second reservoir configured to receive the solvent so that, when received into the first reservoir, the solvent makes contact with the skin of the subject, and a second electrode positioned above the second reservoir; discharging a solvent from at least one vessel to mix with a first powdered agent and enter the anode apparatus; discharging the solvent from the at least one vessel to mix with a second powdered agent and enter the cathode apparatus; and generating a therapeutic direct electrical pulse having a first charge that creates an electrical voltage difference between the first electrode and the second electrode to transport the charged therapeutic agent through the skin of the subject.

The method can further comprise generating a depolarizing electrical pulse by a depolarizing electrode in contact with the skin, the depolarizing electrical pulse having an electric charge opposite of an electric charge on the surface of the skin to depolarize the skin of the subject.

The hair of the subject in the first position on the skin can be epilated prior to securing the anode apparatus to the epilated area of the skin of the subject.

The hair of the subject can be epilated by sugaring.

The method can further comprise epilating the skin by sugaring.

The first powdered agent can be one of neostigmine, glycopyrrolate, fentanyl, alendronate, insulin, citric acid, lidocaine, vitamin B12, sumatriptan, or any other ionizable therapeutic substance.

A duration of the therapeutic electrical pulse can be determined at least in part by settings of a controller device in communication with the first electrode and the second electrode.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIG. 1A is a schematic illustrating an example top side of a wireless iontophoresis patch according to an embodiment of the invention;

FIG. 1B is a schematic illustrating an example bottom side of a wireless iontophoresis patch according to an embodiment of the invention;

DETAILED DESCRIPTION

Figure 2:
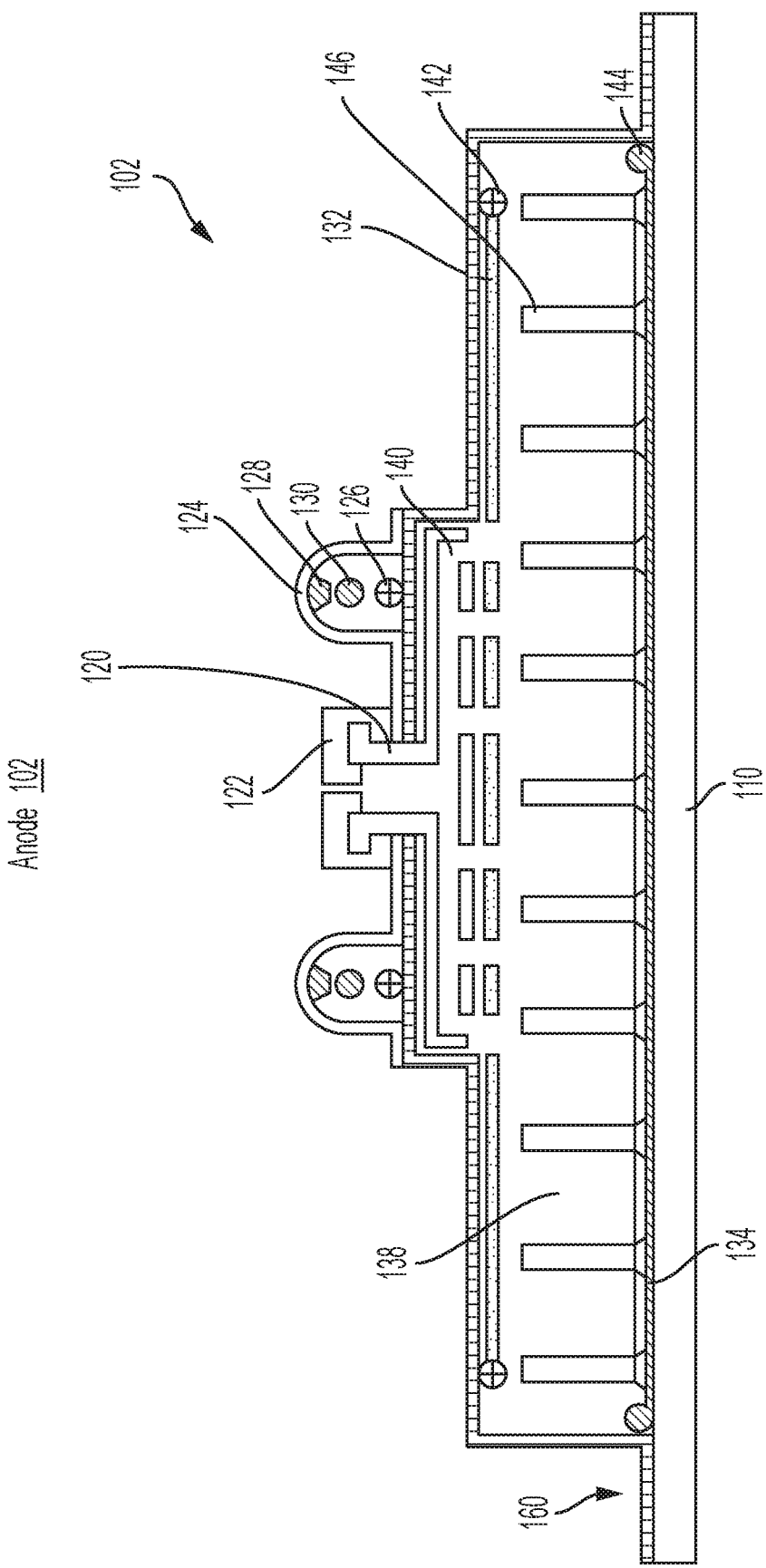
FIG. 2 is a cross sectional view of an example anode apparatus on the skin of a subject according to an embodiment of the invention.

The present invention now will be described more fully hereinafter with reference to the accompanying drawings, in which some, but not all, embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a reservoir" can refer to one or more of such reservoirs, and so forth.

All technical and scientific terms used herein have the same meaning as commonly understood to one of ordinary skill in the art to which this invention belongs unless clearly indicated otherwise.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of" For example, "at least one of A, B and C" explicitly includes only A, only B, only C, and combinations of each.

The word "or" as used herein means any one member of a particular list and also includes any combination of members of that list.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, when values are approximated by the use of the antecedent "approximately," "generally," or "substantially," it is contemplated that values within up to 15%, up to 10%, up to 5%, or up to 1% (above or below) of the particularly stated value can be included within the scope of those aspects.

It should be understood that references herein to "top," "bottom," "above," and "below" should be understood to be descriptive with respect to components' orientations as shown in the Figures. Such references should not be understood to limit the orientations of the components to the embodiments shown. For example, the iontophoresis patches can be inverted so that the "top" and "bottom" ends are reversed. Similarly, in various embodiments, the iontophoresis patches can extend horizontally, vertically, or at any other angle with respect to the ground.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Certain embodiments disclosed herein provide for an improved iontophoresis method delivered by a wireless iontophoresis patch system. According to some aspects, the improved method disclosed herein allows for the iontophoresis system to periodically depolarize the skin of the subject during iontophoresis, thereby negating the skin's electrical counter-polarization reaction to iontophoresis and improving the effectiveness of drug delivery using iontophoresis. Thus, this approach can permit the application of a lower voltage, diminish redness/irritation of the skin due to local histamine release, and/or diminish the possibility of causing a thermal burn to the skin. The intermittent measurement of resistance of the electric current and/or light absorbance by the medication solution remaining within the electrode reservoir can allow for an accurate estimation of the amount of medication in solution (i.e., the amount of medication/ions present in the reservoir can be inversely related to the electrical resistance measured); this approach (e.g., measuring electrical resistance of the solution in the reservoir) can be used to determine the total amount of medication delivered and/or the amount of medication that remains to be delivered. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

FIG. 1A is a schematic illustrating an example top side of a wireless iontophoresis patch 100 according to an embodiment of the invention. In the illustrated embodiment, the wireless iontophoresis patch comprises an anode apparatus 102, a cathode apparatus 104, and a controller device 106 that is electrically connected to the anode apparatus and the cathode apparatus. The controller device is also configured to control the operation of electrodes in the anode apparatus and the cathode apparatus. In one embodiment, the controller device is selectively attachable or detachable. The wireless iontophoresis patch 100 is positioned on the skin 110 of a subject. In one embodiment, the wireless iontophoresis patch is affixed to the skin by way of an adhesive. In some optional aspects, acrylic, syanoacrylates, silicone, polyurethane or other polymer-based hypoallergenic medical adhesives may be employed as adhesive materials. In one embodiment, the wireless iontophoresis patch is at least partially covered by an adhesive covered material, such as, for example, a cloth or a, elastic solid or foam film, and the adhesives can affix the wireless iontophoresis patch to the skin of the subject.

FIG. 1B is a schematic illustrating an example bottom side of a wireless iontophoresis patch according to an embodiment of the invention. In the illustrated embodiment, the wireless iontophoresis patch also includes a non-conducting insulator bridge 108 that can be made of any number of porous, breathable materials such as cotton, polyester, nylon, silk, polyurethane etc. The insulator bridge 108 can be positioned on the skin of the subject between the anode apparatus 102 and the cathode apparatus 104. The insulator bridge 108 provides electrical and physical insulation between one or more electrodes of the anode apparatus 102 and one or more electrodes of the cathode apparatus 104. Optionally, it is contemplated that at least a portion of the insulator bridge 108 can underlie the controller device 106 when the controller device is coupled or attached to the patch 100.

FIG. 2 is a cross sectional view illustrating an example anode apparatus 102 on the skin 110 of the subject according to an embodiment of the invention. In the illustrated embodiment, the anode apparatus comprises a female Luer Lock connector 120 and a silicone slit valve 122. These allow a medicine container with an appropriate companion Luer Lock or any other type of a connector to attach to the anode apparatus 102 and discharge a fluid via a solution distribution channel 140 into the reservoir 138 (e.g., an absorptive mesh/open cell foam) and ultimately to the skin 110 of the subject.

The anode apparatus also includes a controller guiderail and contacts housing 124 that houses a first electrode (anode) contact 126, a second electrode (cathode) contact 128, and a depolarizer electrode contact 130. These contacts facilitate electrical connection and communication between the elements of the anode apparatus 102 and the controller device 106 and the cathode apparatus 104.

The anode apparatus 104 also includes a first electrode (e.g., an Ag/AgCl anode) 132 and a depolarizer electrode 134. The first electrode (e.g., an Ag/AgCl anode) 132 is positioned above the reservoir 138 with respect to the skin 110 of the subject and is electrically connected to the anode contact 126 via an anode wire bus 142. The depolarizer electrode is positioned below the reservoir 138 and is adjacent to and in physical contact with the skin 110 and is electrically connected to the depolarizer contact 130 via a depolarizer bus wire 144.

The anode apparatus also includes a vertical spacer 146. The vertical spacer 146 may be made from LDPE plastic or any other suitable plastic or other material. The vertical spacer 146 functions to maintain a desired distance between the first electrode and the depolarizing electrode. The vertical spacer 146 also functions to maintain consistency in the volume of the reservoir and to provide consistency with respect to resistance readings involving the reservoir. The spacer 146 can be organized in a grid form and can comprise horizontal connecting members located proximate the skin and projecting vertically within the absorptive mesh of the reservoir 138.

Finally, both the anode and cathode apparatus may be partially or completely covered in an adhesive covered material 160, such as, for example, cloth or an elastic material, to allow the adhesive to affix the anode apparatus 102 and the cathode apparatus 104 as a combined unit to the skin 110 of the subject.

Figure 3:
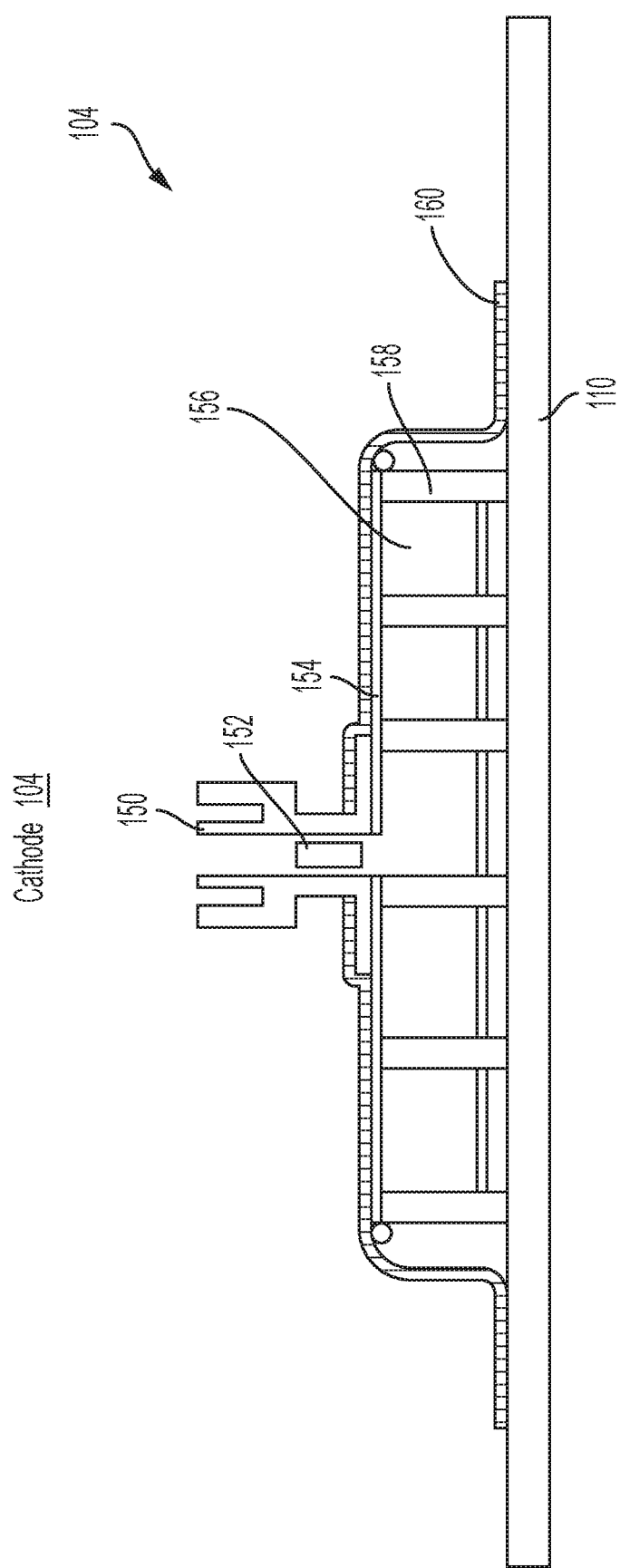
FIG. 3 is a cross sectional view of an example cathode apparatus on the skin of a subject according to an embodiment of the invention.

FIG. 3 is a cross sectional view illustrating an example cathode apparatus 104 on the skin 110 of a subject according to an embodiment of the invention. In the illustrated embodiment, the cathode apparatus 104 comprises a male Luer Lock 150 or any other type of a connector and a bi-directional valve 152. These allow a solution container with an appropriate companion connector to attach to the cathode apparatus, to remove air and to deliver a fluid via the valve into the reservoir 156 (e.g., an absorptive mesh/open cell foam) and ultimately to the skin 110 of the subject.

The cathode apparatus 104 also includes a second electrode (e.g., an Ag/AgCl electrode) 154. The second electrode (e.g., an Ag/AgCl electrode) 154 can be positioned above the reservoir 156 with respect to the skin 110 of the subject and is electrically connected to the cathode contact 154. The cathode apparatus also includes a spacer 158 that may be made from LDPE plastic or any other suitable non-conductive material. The spacer functions to maintain a desired distance between the first electrode and the skin of the subject. The spacer also functions to maintain consistency of the volume in the reservoir. The spacer 158 can be organized in a grid and can comprise horizontal connecting members located proximate the skin.

Figure 4:
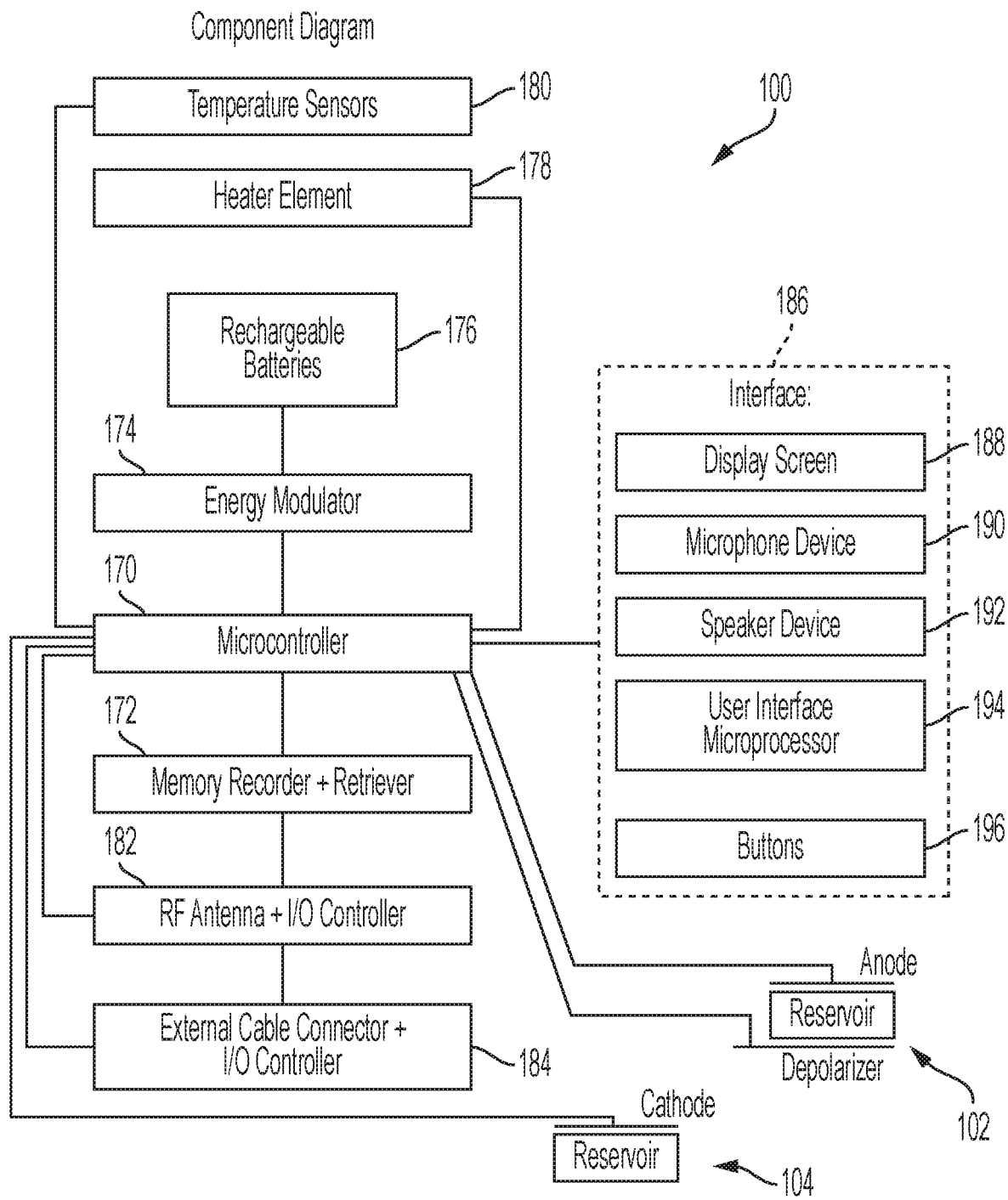
FIG. 4 is a block diagram illustrating an example wireless iontophoresis patch according to an embodiment of the invention.

FIG. 4 is a block diagram illustrating an example wireless iontophoresis patch according to an embodiment of the invention. In the illustrated embodiment, the wireless iontophoresis patch comprises a microcontroller 170 or other processor. Under the control of the processor in the illustrated embodiment are a memory 172, an energy modulator 174 coupled with rechargeable batteries 176, a heater element 178, one or more temperature sensors 180 and/or other sensors, a radiofrequency (RF) antenna and input/output controller 182, an external cable connector and input/output controller 184, the anode apparatus 102, and cathode apparatus 104. The controller also controls a user interface 186 that in the illustrated embodiment includes a display screen 188, a microphone device 190, a speaker device 192, a separate user interface microprocessor 194 and one or more physical input devices 196 such as buttons, digitizer screens, keyboards and mice and the like.

Figure 5:
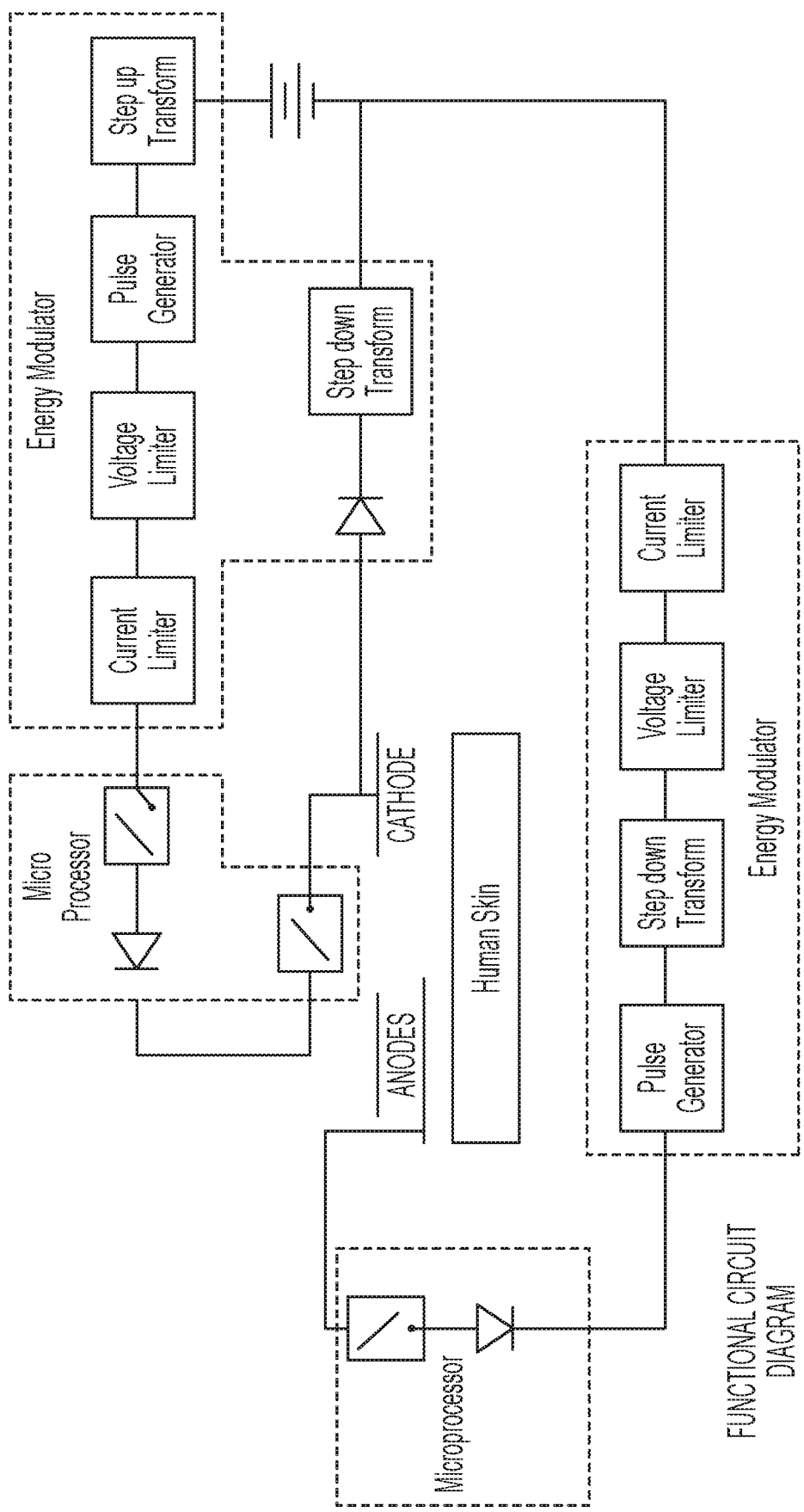
FIG. 5 is a block diagram illustrating an example circuit diagram for a wireless iontophoresis patch according to an embodiment of the invention.

FIG. 5 is a block diagram illustrating an example circuit diagram for a wireless iontophoresis patch according to an embodiment of the invention.

Figure 6:
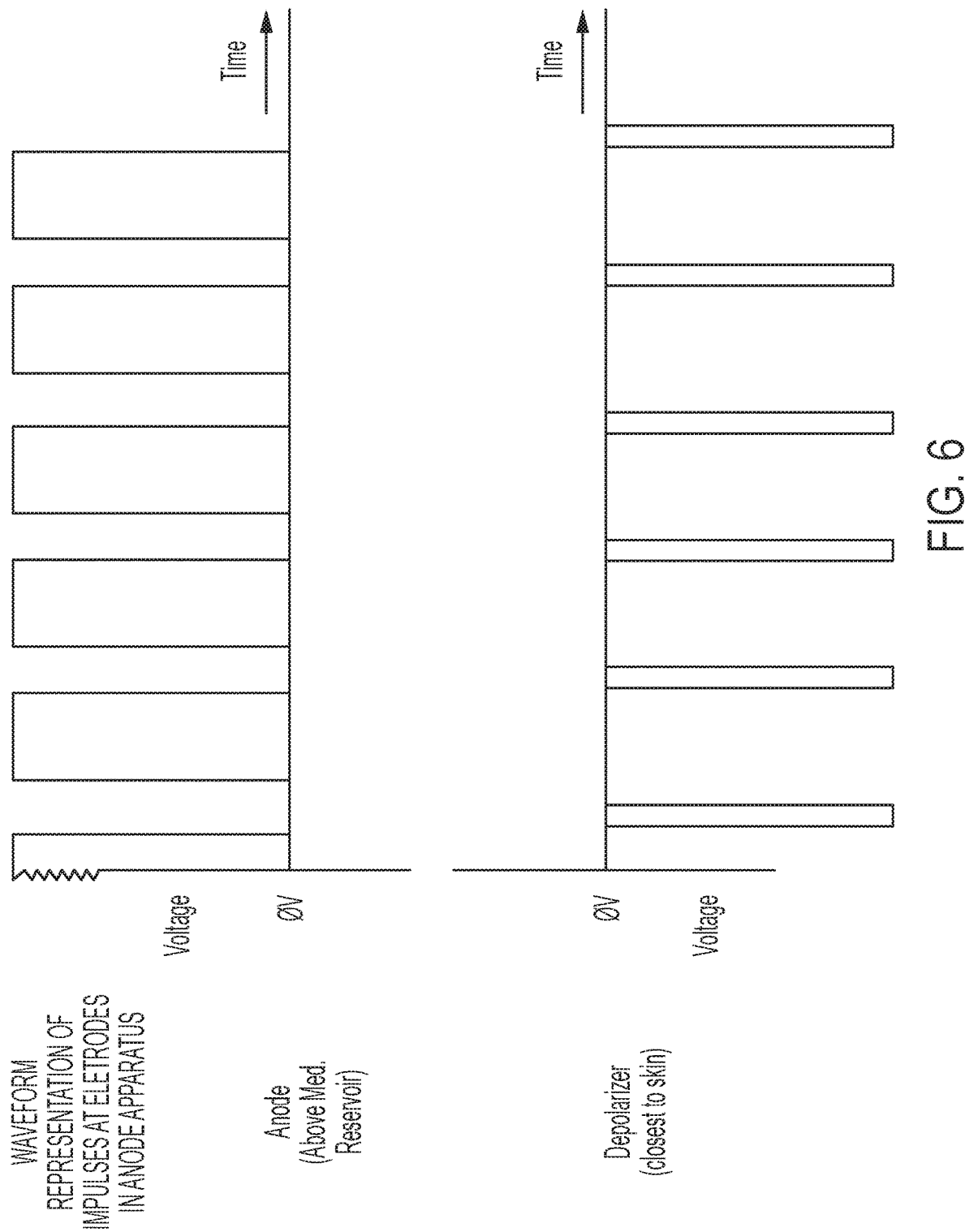
FIG. 6 is a waveform diagram illustrating example electrical impulses in an anode apparatus during improved iontophoresis according to an embodiment of the invention.

FIG. 6 is a waveform diagram illustrating example electrical impulses in an anode apparatus during improved iontophoresis according to an embodiment of the invention. In the illustrated embodiment, under control of the controller device, the first electrode of the anode apparatus periodically generates a therapeutic electrical pulse to transport a charged therapeutic agent through the skin of the subject. In one embodiment, the therapeutic electrical pulse has a first charge and a first electron flow direction. Additionally, under control of the controller device, the depolarizer electrode of the anode apparatus periodically generates a depolarizer electrical pulse to depolarize the skin of the subject. In one embodiment, the depolarizer electrical pulse has a second charge that is opposite in value to the first charge. As shown in the diagram, the depolarizer electrical pulses are generated when the therapeutic electrical pulses are at zero volts and the therapeutic electrical pulses are similarly generated when the depolarizer electrical pulses are at zero volts. This advantageously allows the skin to depolarize in brief intervals between the longer therapeutic electrical pulses to increase the effectiveness of iontophoresis at delivering ionized medications into the systemic circulation of the subject.

Figure 7:
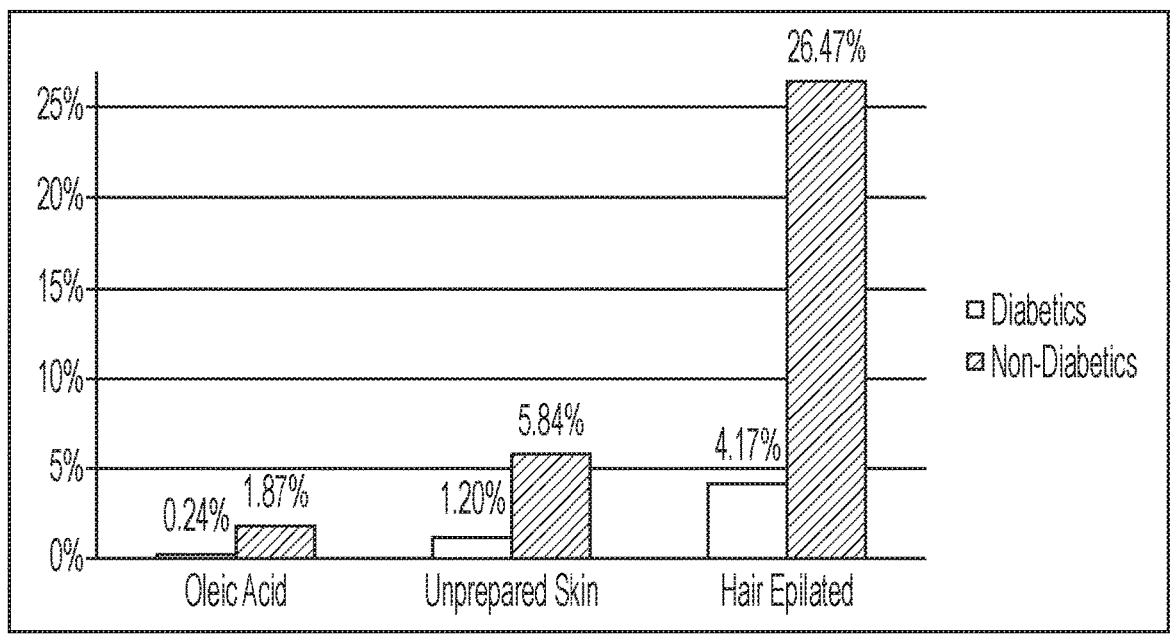
FIG. 7 is a graph diagram illustrating comparative effectiveness of improved iontophoresis in delivering ionic substance into the circulation using alternative skin preparations according to an embodiment of the invention.

FIG. 7 is a graph diagram illustrating comparative effectiveness of improved iontophoresis using alternative skin preparations according to an embodiment of the invention. A surprising and outstanding result of the improved iontophoresis method was observed when the hair on the skin of the subject is epilated prior to iontophoresis. In some embodiments, prior to application of the disclosed patch (and initiation of iontophoresis), the hair can be epilated via sugaring (e.g., using cloth, paper, or film strips). As compared to epilating with wax, glues, tapes, etc., sugaring can maintain integrity of the skin's stratus corneum while epilating the hair shafts. This can provide optimized safety during iontophoresis.

Figure 8:
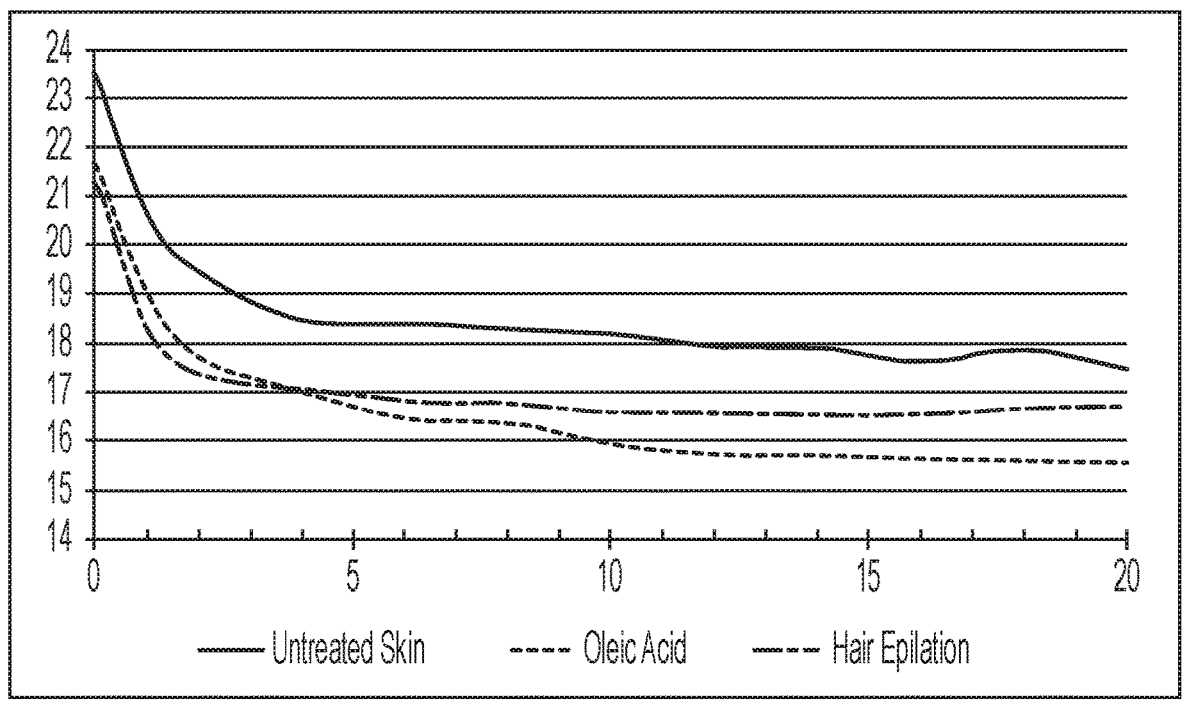
FIG. 8 is a graph diagram illustrating comparative amounts of voltage required to maintain the same current for improved iontophoresis using alternative skin preparations according to an embodiment of the invention.

FIG. 8 is a graph diagram illustrating comparative amounts of current required for improved iontophoresis using alternative skin preparations according to an embodiment of the invention. A surprising and outstanding benefit was observed to be that less current is required for effective iontophoresis when the hair on the skin of the subject is epilated prior to iontophoresis.

Figure 9:
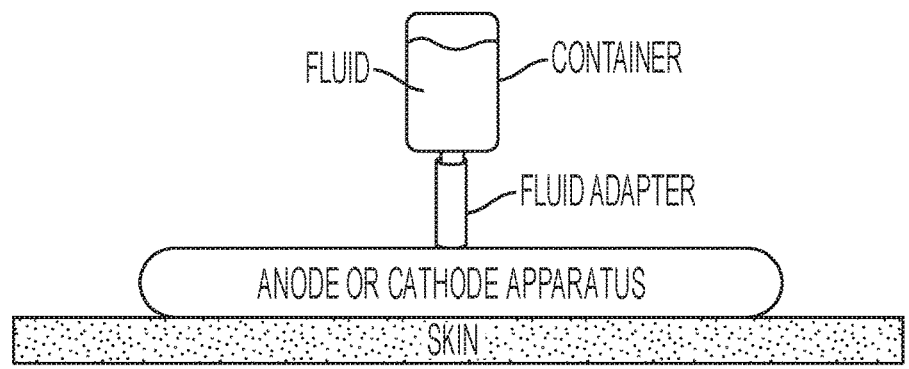
FIG. 9 is a schematic diagram illustrating an example delivery system for a wireless iontophoresis patch according to an embodiment of the invention.

FIG. 9 is a schematic illustrating an example delivery system for a wireless iontophoresis patch according to an embodiment of the invention. In the illustrated embodiment, the anode or cathode apparatus has an integrated fluid adaptor. As previously discussed, in some embodiments, this may manifest as a male or female Luer Lock connector. Advantageously, the wireless iontophoresis patch can employ a different style of integrated adaptor on each of the anode apparatus and the cathode apparatus to prevent misapplication of the different fluids to the wrong anode apparatus or cathode apparatus of the wireless iontophoresis patch.

Referring to FIGS. 11-13B, according to a first embodiment of the iontophoresis system, a controller 200 (FIGS. 12-13B) can be mated with the patch 202 in a secure and reversible manner. The patch 202 can comprise a plug 252 extending vertically from the patch 202. The controller can comprise a socket 248 that is configured to receive (e.g., matingly receive) the plug 252. The patch 202 can be disposed on the skin of the patient, and the controller 202 can be placed on top of the patch 202 (i.e. spaced from the skin) and slid horizontally into engagement so that the socket 248 engages the plug 252. A pair of detents 250 can secure the plug 252 to the socket 248 so that the patch 202 and controller 200 are mechanically coupled. In this way, the patch 202 and controller 200 can be connected in a configuration that enables electrical communication between respective electrical contacts. Moreover, the coupling between the plug 252 and socket 248 can physically position respective mechanical components such that they can interact as further disclosed herein. For example, the coupling between the plug 252 and socket 248 can position the rack in vertical and horizontal alignment with the circular pivoting gears, as discussed further below.

Figure 13A:
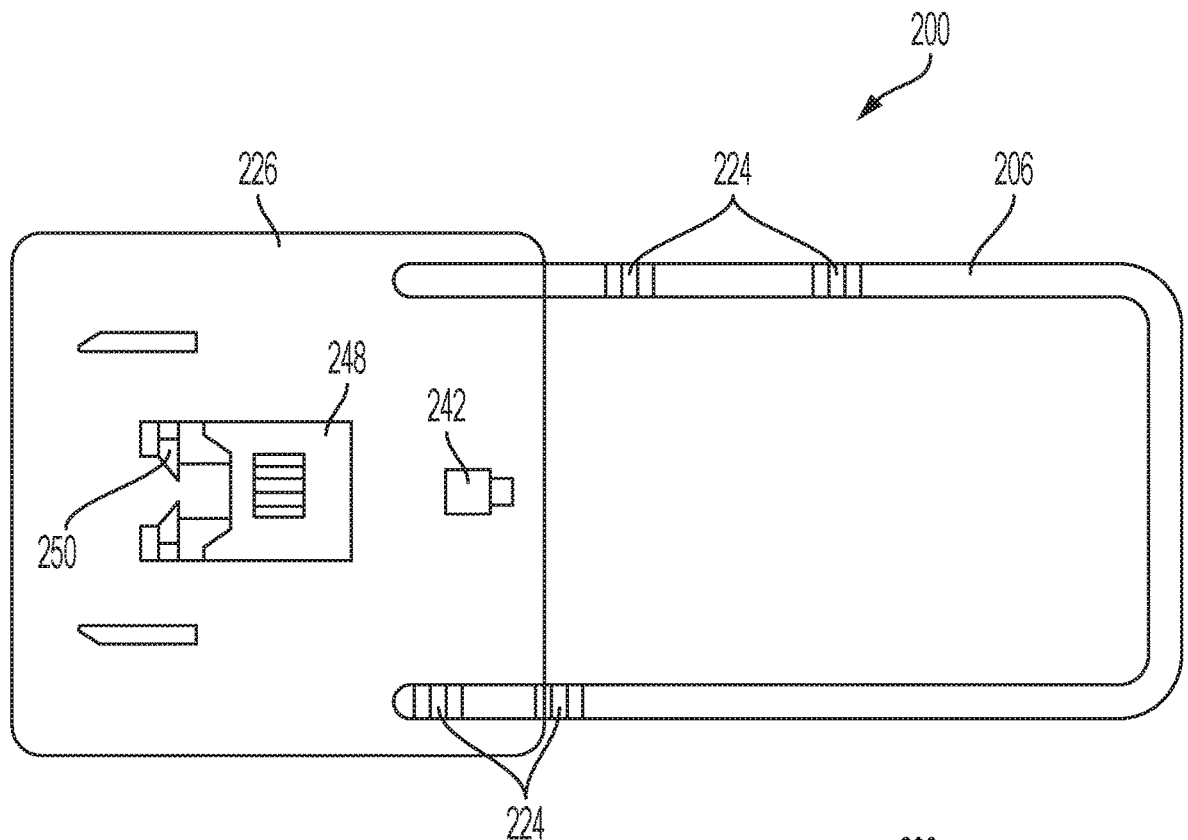
FIG. 13A is a top view of the controller of FIG. 12 in an open configuration.
Figure 13B:
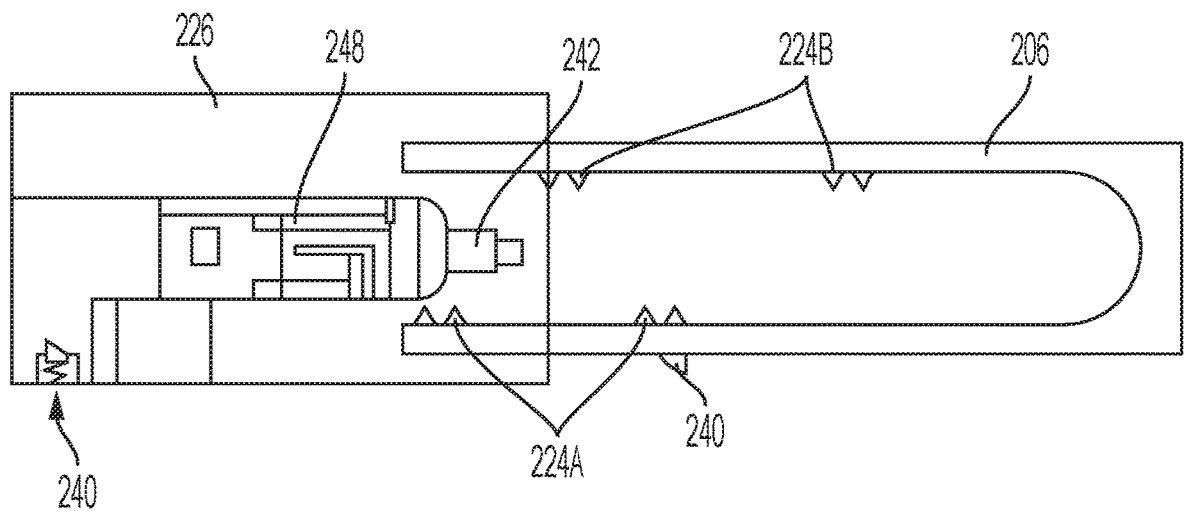
FIG. 13B is a side view of the controller of FIG. 13A.

The patch 202 can contain an aggregate of lyophilized medication, solvent, buffer, and conduits to the reservoirs for transcutaneous drug delivery. The patch can be attachable to the skin by an adherent patch sheet 204. The controller 200 can have a tray 206 that is slidable with respect to a controller body. The tray 206 can comprise longitudinally extending a pair of rails on either side, one above and one below, having linear gears, or racks 224, thereon for actuating a pinion, or circular pivoting gears 218, that turn a drum 216 to actuate needles 210, as described further below. The patch 202 can mate with the controller with the controller's tray 206 in fully extended, or open, position (FIG. 13A). The patch 202 can contain the anode electrode 132 (FIG. 2) and a cathode electrode 154 (FIG. 3), each with a respective underlying mesh and spacer grid 158, described above with reference to FIGS. 2 and 3, between the respective conductive surfaces and the skin, which can reduce the likelihood of skin burns. The medication(s) and buffer can be contained in a chamber 222 or contained on the surface of the mesh of one of the reservoirs 138 and 156. A negative pressure can be created in the reservoirs to facilitate the introduction of solvent to each reservoir 138 and 156. Moreover, the negative pressure can remove air so that the solvent can evenly fill the reservoir to fill the contact area. It should be understood that excessive air in the reservoir can reduce contact area with the patient, thereby increasing current through the smaller areas of skin, which can lead to burns. To create the low pressure in the reservoirs 138 and 156, a vessel 207 with negative pressure can be punctured by separate needles 210 connected to the anode and cathode reservoirs. The patch 202 can comprise two vessels 207, 208 having respective diaphragm caps 220 that are positioned to directly face the needles 210. The vacuum vessel can first be punctured by respective needles connected to separate tubes 212 leading to the anode and cathode reservoirs 138 and 156. Subsequently, the solvent vessels can be punctured by respective needles connected to separate tubes 212 leading to the anode and cathode reservoirs 138 and 156 to deliver solvent to the respective reservoirs. The needles 210 can puncture each chamber in succession, as described below. The needles 210 that puncture the vessel can be capped with an elastic material-sheath 214 to fluidly seal the system when withdrawn from each vessel 207, 208. As the solvent mixes with the medication(s), the solvent and medication(s) can mix to form a solution. The same process can be performed (optionally, simultaneously or concurrently performed) with the buffer powder. The patch 202 can comprise a pair of drums 216 that rotate to cause reciprocal movement of the needles. The needles 210 can slide within a channel, with each needle 110 being connected to the drum by an extensible connector. As bottom racks 224A on rails of the tray 206 engage the respective bottoms of the circular gears 218, the needles can move to puncture the chamber cap 220. Subsequently, top racks 224B of the tray 206 can engage the respective top of each geared drum 218, causing the needles 210 to retract until the needles 210 are withdrawn from the chamber cap 220. The drums 216 can be rotationally fixed to respective circular pivoting gears 218 so that as the circular pivoting gears engage respective racks 224 on the tray 206, the circular pivoting gears 218 can rotate (i.e., as a rack and pinion system), thereby causing the respective drums 216 to rotate.

To deliver medication by iontophoresis using the first embodiment of the iontophoresis system, the user can apply lateral pressure, sliding the tray 206 towards the controller body 226. Each side of the tray 206 can have rails that pass through the frame 228 of the patch 202, one passing above and one passing below circular gears 218 of the rotating drums 216. Each of the four rails (two per geared drum) can be equipped with one set of racks 224. In a specific sequence, these racks 224 can engage the respective rotating drum 218, either on top or on the bottom, thereby rotating each drum and moving the sheathed needles 210 either through the vessel diaphragms 220 or out of the vessels 207, 208. This action can initially evacuate air from both the anode reservoir 138 and the cathode reservoir 156 via the low pressure source of vessel 207. When withdrawn from the vessels, the elastic sheathes 214 on the needles 210 can seal the vacuum. The water vessel 208 can contain a quantity of deionized water that equals the combined volume of the anode and cathode reservoirs. It can also contain an elastic pressurized gas sphere 232 (or air balloon) submerged in the deionized water and held away from the diaphragm 220 by the tapered shape of the vessel 208. The two needles 210 that are attached to the tubing can puncture the solvent vessel 208, thereby allowing fluid to flow via tubes 212 into one of the chamber 222 having lyophilized medication therein or the chamber 222 having buffer therein. The contents of these tubes can continue to flow into the appropriate anode reservoir 138 or cathode reservoir 156. As the user continues to advance the tray 206 towards the controller body 226 the needles 210 can be withdrawn from the solvent vessel 208 and be sealed by the elastic needle sheaths, closing system. When the tray 206 is advanced to its limit, it can be locked in the closed position via a spring-loaded catch 240, simultaneously engaging the switch 242, which can permit the controller to become capable of delivering current to the electrodes in a pre-programmed fashion. Optionally, a switch in communication with the controller can enable a user to start/stop the therapy. At the time of completion of medication delivery, the controller can emit an audible sound to signify the completion of therapy and the need to remove the patch from the skin.

Figure 14:
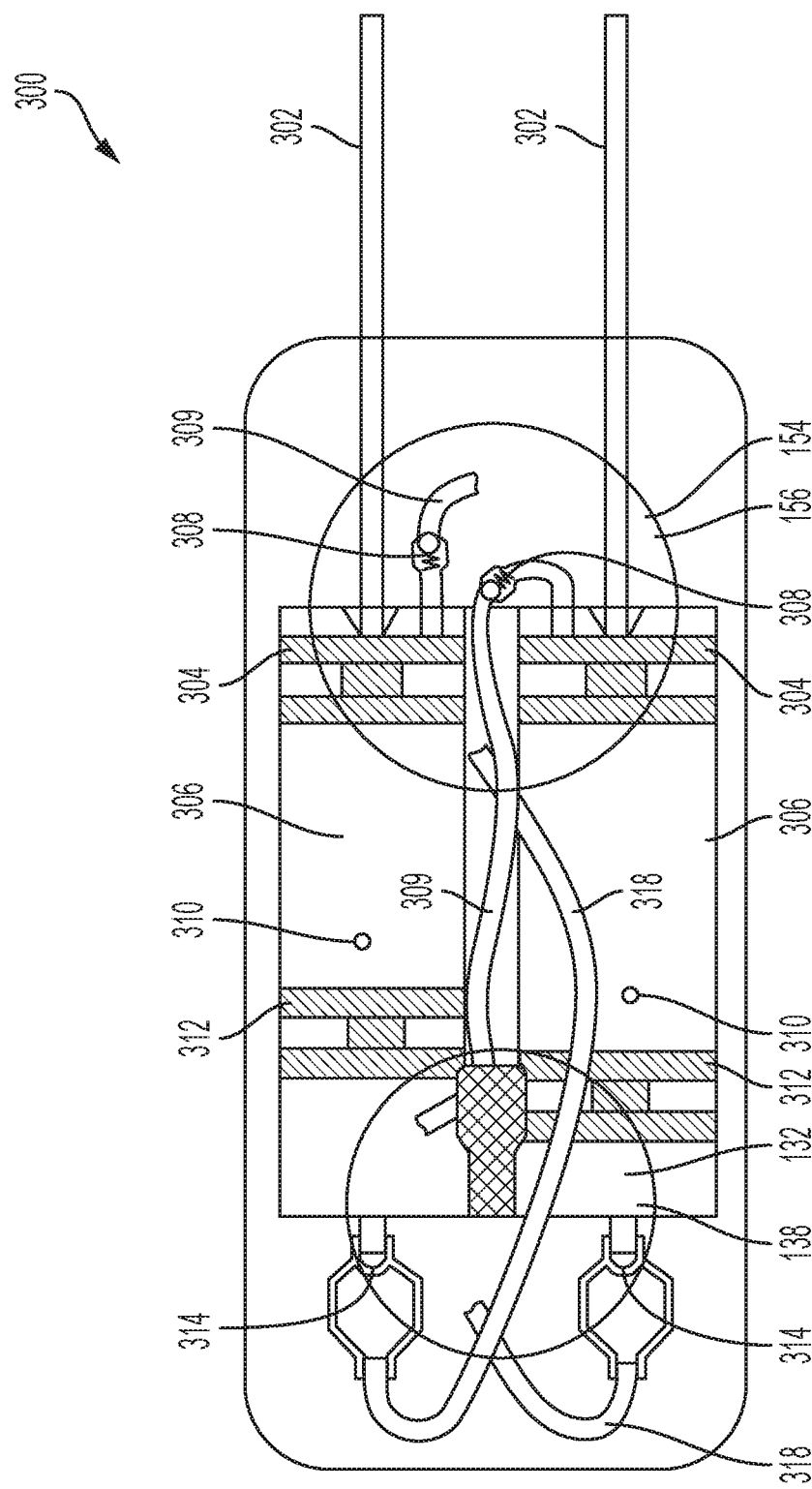
FIG. 14 is a top view of another embodiment of an iontophoresis patch.
Figure 15A:
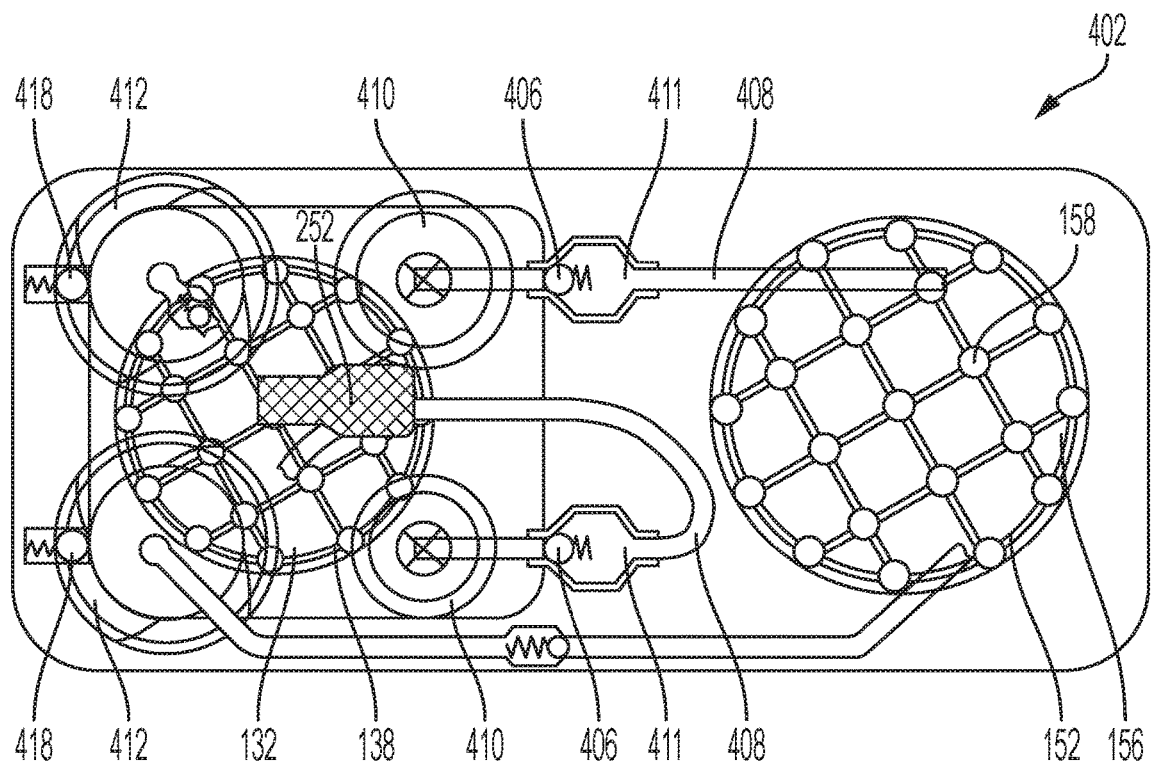
FIG. 15A illustrates a top view of another embodiment of an iontophoresis patch
Figure 15B:
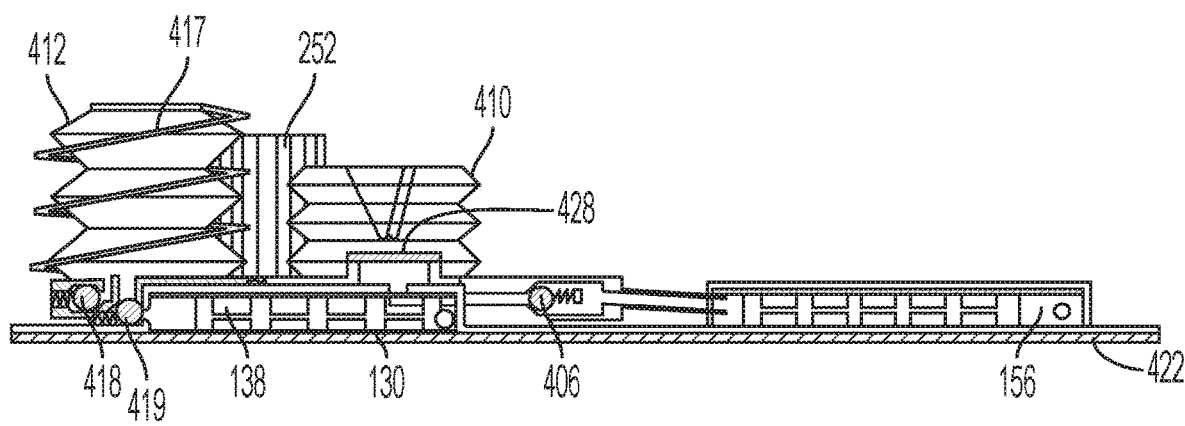
FIG. 15B illustrates a side view of the embodiment of the iontophoresis patch of FIG. 15A.
Figure 16A:
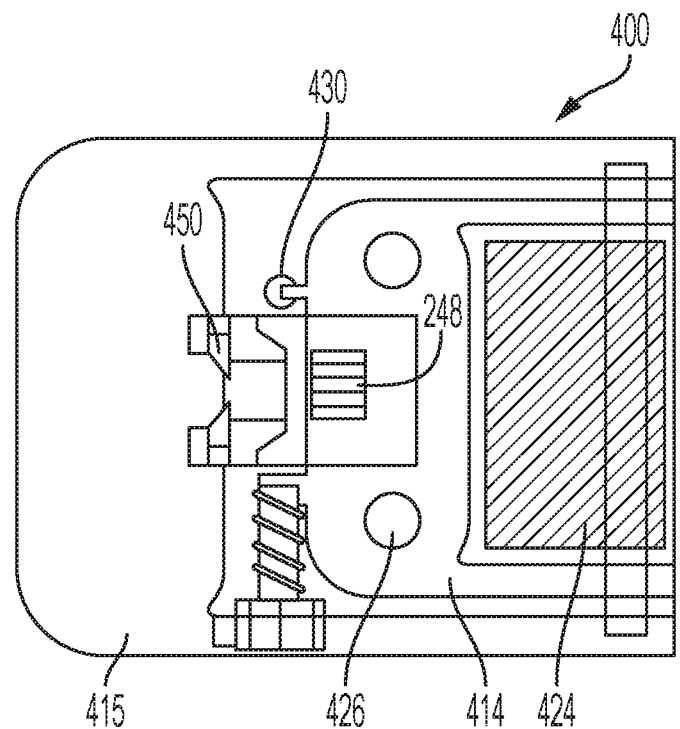
FIG. 16A illustrates a top view of a controller for use with the iontophoresis patch of FIG. 15A.
Figure 16B:
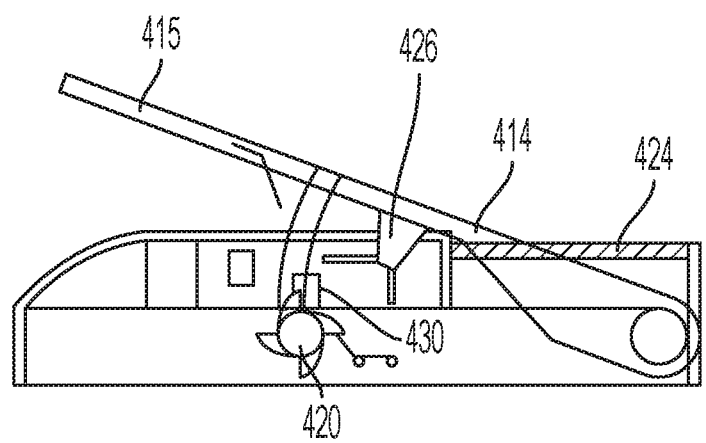
FIG. 16B illustrates a side view of the controller of FIG. 16A.

Referring to FIGS. 13A-14, according to a second embodiment of the iontophoresis system, the detachable iontophoresis controller 200 (FIG. 13A) can be adapted to accept a patch 300 with two integral or removable syringes. A handle of the tray 206 that extends transversely between the rails can engage the syringe plunger rods 302. The syringes can be pre-loaded (e.g., with solvent) in portions of syringe tubes 306. The installation/mating between the iontophoresis controller 200 and the patch 300 can establish a secure physical connection. When the user slides the tray towards the controller 200, a surface of the tray 206 can bias against syringe rods 302 to move both plungers 304 forward through respective syringe tubes 306, thereby creating a partial vacuum and aspirating air from the anode reservoir 138 and the cathode reservoir 156 through one-way valves 308 and tubes 309. As the user continues to slide the tray 206 forward, the plunger 304 can pass fenestrations 310 in the cylinder walls of the lower part of the syringe, thereby breaking the vacuum in the syringe tubes. The reservoirs can be sealed by closing of the one-way valves 308. Thereafter, each plunger 304 can push a respective second plunger 312. Pressure on the liquid inside the syringe can break a scored metal diaphragm 314 and inject solvent into chambers 316 with lyophilized medication(s) or buffer. Placing the medications into chambers 316 that are able to be substituted for other chambers allows for interchangeability with other medications or additional doses of medication to be introduced prior to removal of the patch from the skin. Further movement of each plunger 304 can deliver the solutions to the respective reservoirs 138, 156 through tubes 318.

To deliver medication by iontophoresis, as the user continues to advance the tray 206 toward the controller 200, a portion of the tray 206 can come into contact with and actuate a button 242. The button 242 can be in communication with the microcontroller 170 (FIG. 4) of the controller 200 and can activate the system. After actuating the button 242, the tray 206 can then be locked in place, which can allow for the system to deliver electric current for administration of medication(s). According to an optional aspect, programming of the controller can be possible before or after the charging of the patch. The user can be able to choose the dose of medication to be delivered by setting the number on a graphic user interface screen, that is responsive to point pressure and/or heat/touch of the human body part, such as finger, or by a voice command via a microphone that is an integral component of the controller, or through a remote wireless device.

Referring to FIGS. 15A-16B, according to a third embodiment of the iontophoresis system, a controller 400 can be mated with the patch 402 in a secure and reversible manner. As described with reference to the first embodiment, the controller 400 can comprise a socket 248. The patch 402 can comprise a matching plug 252 that is receivable (e.g., matingly receivable) into the socket 248. The socket 248 can comprise detents 250 that can releasably secure the plug 252 and, therefore, the patch 402 to the controller 400. In this way, the patch 402 and controller 400 can be connected in a configuration that enables electrical communication between respective electrical contacts. Moreover, the coupling between the plug 252 and socket 248 can physically position respective mechanical components such that they can interact as further disclosed herein. For example, the coupling between the plug 252 and socket 248 can position the accordion chambers in alignment with the pedals, as discussed further below. Accordingly, the patch 402 and controller 400 can be coupled in an orientation in which the patch 402 is positioned on the subject's skin, and the controller is positioned above the patch 402.

The patch 402 can contain an aggregate of lyophilized medication, solvent, buffer, and conduits to the reservoirs for transcutaneous drug delivery. The patch 402 can comprise two resilient, elastic accordion chambers 410 having solvent therein and two vacuum elastic accordion chambers 412 that are configured to remove air from respective reservoirs 138, 156. The anode reservoir 138 and the cathode reservoir 156 can be in fluid communication, through tubes 408 having one-way valves 406 therein, to the accordion chambers 410 (e.g., blebs). The solvent accordion chambers 410 and vacuum accordion chambers 412 can be compressed by the movement of a solvent pedal 414 and a vacuum pedal 415, respectively. The solvent pedal 414 and vacuum pedal 415 can be hinged flaps on the superior surface of the controller 400. Tubes 408 can conduct solvent through respective lyophilized medication/buffer chambers 411. Alternately, the electrode reservoirs 138, 156 can contain lyophilized medication or buffer (obviating the need for separate medication or buffer chambers 411). The vacuum pedal 415 can be spring-loaded via a spring 417 and can create a vacuum in the reservoirs 412 by aspiration and expulsion of air through respective one-way valves 418 and 419. The solvent pedal 414 can then deliver solvent through chambers 411 with medication(s) or buffer therein and deliver the resulting solutions to the respective anode reservoir 138 and cathode reservoir 156. The vacuum pedal 415 can rotate a ratchet 420 on a rod that can turn a set fraction of a complete rotation with each compression. The ratchet 420 can actuate a release that can unlock the solvent pedal 414 after a set number of compressions. That is, the vacuum accordion chambers 412 can be pumped a number of times to remove air from the reservoirs 138, 156, and sufficient rotations of the ratchet 420 can trigger a release to unlock the pedal 414 for dispensing the medication once the reservoirs 138, 156 are sufficiently vacuumed out.

To deliver medication by iontophoresis with the third embodiment of the iontophoresis system, the user can attach the controller 400 to the patch 402, peel off an adhesive protectant 422 from the underside of the patch, and attach the patch to the skin. The user can optionally then follow the instructions that can appear on a screen 424 of the controller 400 and proceed with filling the patch with medication and buffer solutions. By pressing and releasing the vacuum pedal 415 several times, the user can establish a partial vacuum in the anode 138 and cathode 156 reservoirs. Further, pressing and releasing the vacuum pedal 415 can rotate the ratchet wheel 420 to a position in which it can lock the vacuum pedal 415 that generated a partial vacuum in a closed position as well as release a lock on the solvent pedal 414. As the user depresses the solvent pedal 414, both of the water accordion chambers 410 underneath the solvent pedal 414 can be compressed. Further, the pedal 414 can drive short plastic rods 426 on the underside of the pedal through scored metal diaphragms 428 and allow solvent to flow through tubing 408, dissolving the lyophilized drug and/or buffer powder in the chambers 411 and filling the anode reservoir 138 and cathode reservoir 156. Upon locking the water pedal in the compressed position, a switch 430 can be activated to permit the controller 400 to deliver current to the electrodes 132, 154 in a pre-programmed fashion. Though a secure wireless link, the disclosed iteration of iontophoresis systems can optionally have the capability to be remotely linked to a smart device to initiate the therapy, modify the settings, and to discontinue therapy.

Figure 10:
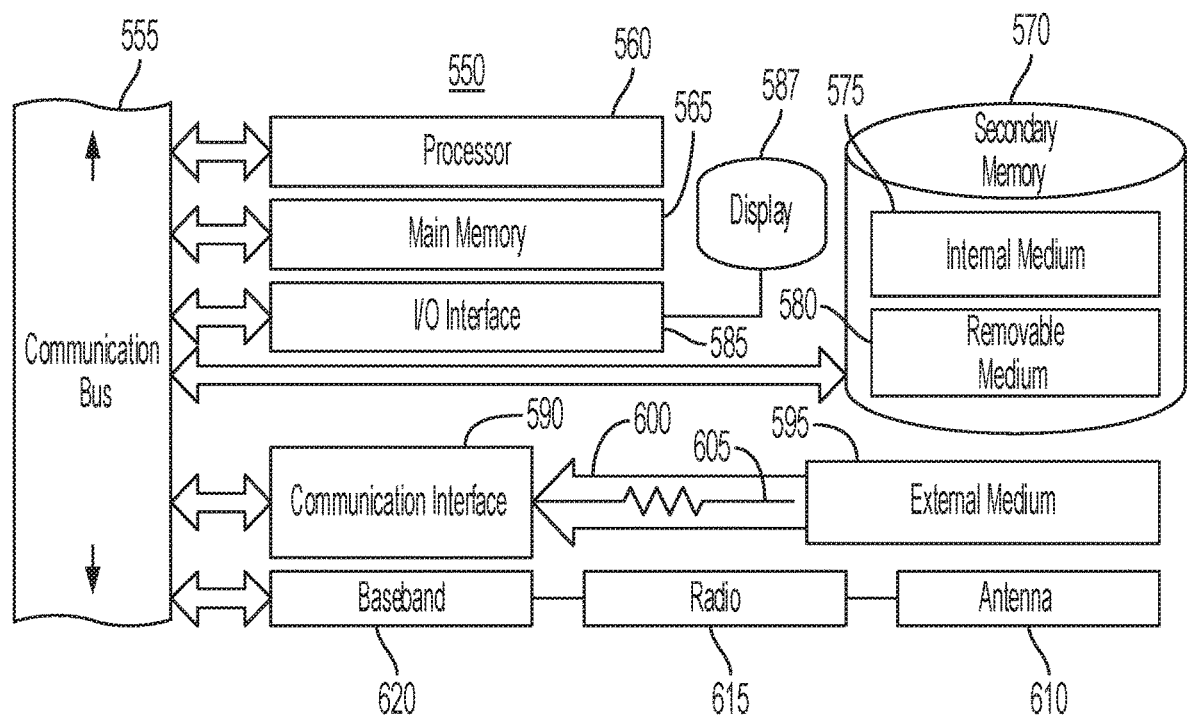
FIG. 10 is a block diagram illustrating an example wired or wireless processor enabled device that may be used in connection with various embodiments described herein.
Figure 11:
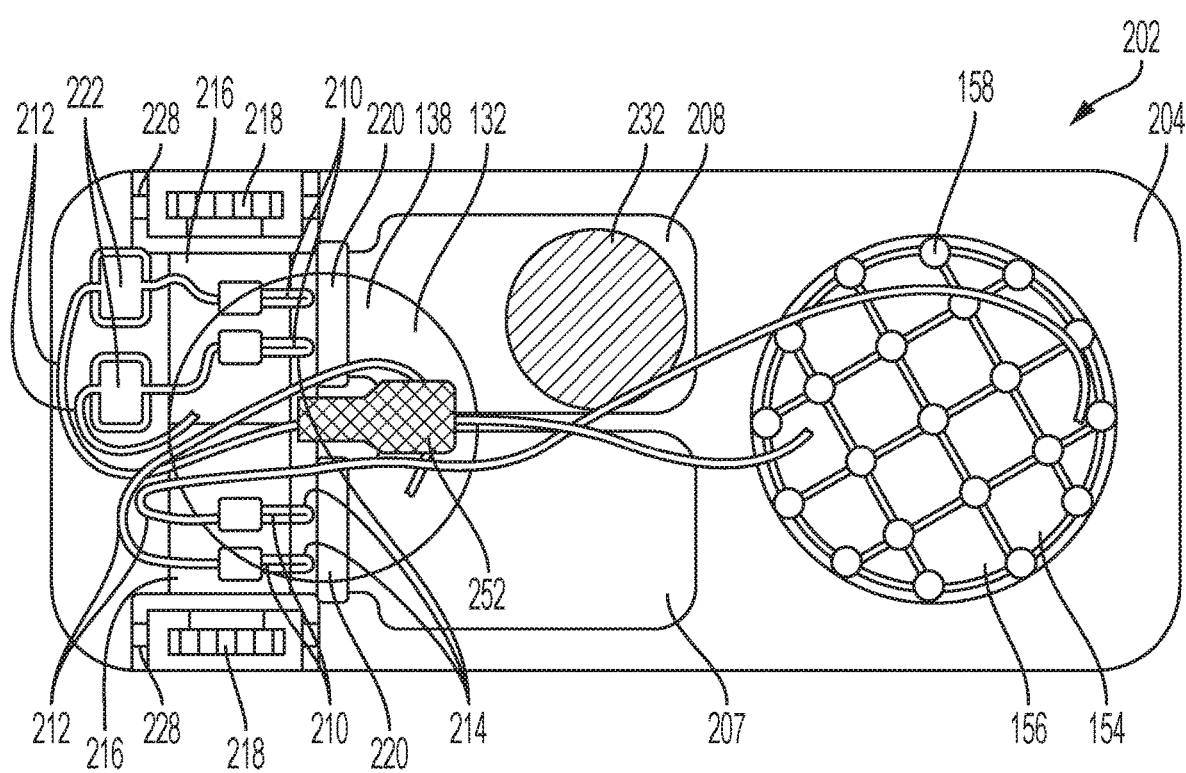
FIG. 11 is a top view of a block diagram of one embodiment of an iontophoresis patch.
Figure 12:
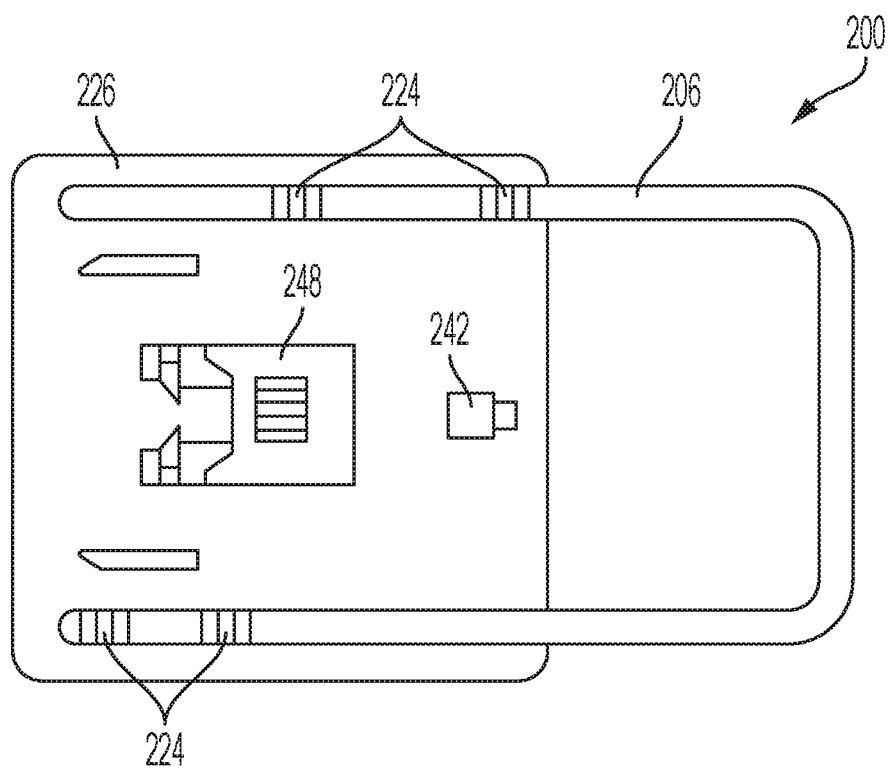
FIG. 12 is a top view of a controller, in a partially closed configuration; for use with the iontophoresis patch of FIG. 11.

FIG. 10 is a block diagram illustrating an example wired or wireless system 550 that may be used in connection with various embodiments described herein. For example, the system 550 may be used as or in conjunction with a controller device or an interface system or its components as previously described herein. The system 550 can be a conventional personal computer, computer server, personal digital assistant, smart phone, tablet computer, smart watch, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include an internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display 587. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

Exemplary Configurations and Methods

According to various aspects, a conductive mesh (depolarizer electrode), in direct contact with the surface of the skin can depolarize the skin with a frequency of 5-50 khz of pulsed DC, operating in unison but phase-offset from harmonically pulsed positive current emitted by the therapeutic anode electrode. The depolarizer electrode can serve as a counter plate to the primary electrode for the goal of estimating the dose of the medications delivered via the measurement of resistivity, or other electrical parameters, between the two plates (intermittently). The electrical property analysis can be conducted according to the pre-programmed reference table present in the memory of the iontophoresis controller for the particular medication/electrolyte combination. Estimated concentrations and dosages remaining according to the table of resistances can be presented on the display screen and/or voiced to the user according to user preferences.

The anode part of the skin patch can operate in the following manner: the top plate can drive the medications while the bottom plate is neutral, and the bottom plate can depolarize the skin while the top plate is neutral. The same pulse generator can generate both the therapeutic pulse and the forced discharge pulse components. In a further embodiment, each pulse can be separately generated by different pulse width modulating generators. A DC bias voltage can be further applied at the top plate electrode, in addition to the pulse voltage, in order to counteract the skin resistivity, within such a range that no, or minimal, skin irritation occurs. This bias current can then serve as the "neutral" level voltage for the Pulse Width Modulating generator. The distance between the electrodes will be maintained constant by the use of an LDPE (or any other fitting type of plastic) spacer mesh so as to allow consistency of the reservoir volume and resistance given an identically-concentrated medication solution.

The patch's Cathode (positive) electrode can have a liquid chamber with a non-conductive mesh or open cell foam capable of fitting 2-5 mL of solution. Silver/silver chloride foil can form the conductor above the mesh and connect to the current source. A field of hypoallergenic medical skin adhesive-impregnated tan colored cloth or elastic plastic foam (polyacrylate or any other fitting material) can surround the mesh. The device can include a patch with two electrodes and one or more reservoirs storing an ionic therapeutic agent, for example, but not limited to, vitamin B12, Neostigmine, Glycopyrrolate, Insulin, Fentanyl, Lidocaine, Alendronate, Sumatriptan, Citric Acid etc. The one or more reservoirs can release the therapeutic agent(s) into the skin of the user when the reservoirs are positioned under the electrodes to form an electrical path for the iontophoretic electro-transport-inducing electrical current. The device can include a detachable electronic controller which delivers current to drive the electrons according to a selected program.

According to some aspects, a patch can be a self-contained unit. The patch can comprise an anode (positive electrode) apparatus. The anode apparatus can comprise an empty chamber with a porous, open-cell foam or mesh pad able to fit 2-5 mL of solution below a silver/silver chloride impregnated aluminum or silver foil but over a thin conductive grid that forms the initial contact with the user's skin. The anode apparatus can further include a female, male Luer Lock or any other liquid transfer adapter with a one or two tubing entrance points (to permit "loading" of the chamber with a water solution containing a quantity of the drug(s) with SLS (sodium lauryl sulfate at [0.2%]) or another fitting ionic surfactant) solution being an optional addition as well as to vacuum out the air. The anode apparatus can comprise vertically stiff but horizontally very pliable LDPE polyethylene (or any fitting type of plastic) horizontal lattice of members interconnecting vertical studs measuring 2-7 mm high and 0.5-2 mm in diameter extending away from the skin at a mesh, foam, or air touching the top Ag/AgCl electrode foil. The studs will serve as a structural limiter for contact between the electrode and the skin, maintaining even electrical resistivity at times when external pressure is applied to the patch, preventing overcurrent controller-initiated shutdowns and skin burns. The cathode can comprise an inferior depolarizing grid electrode made of a conductive material. The anode apparatus can comprise a superior positive anode silver/silver chloride foil electrode.

The cathode apparatus can comprise a reservoir that contains a medication embedded into a hydrogel matrix or be deposited as a fine powder onto a mesh or foam under a removable flexible HDPE or other similar plastic cover/adhesive protector that is continuous and covers the whole underside of the skin patch. Hydrogels based on polyvinyl-alcohol, hydroxypropylmethylcellulose (HPMC), and polyethylene oxide are some of the examples of hydrogels. In some embodiments, the surface area of the cathode can be at least two times as large as the surface area of the positive electrode. The hydrogel or mesh can contain Ag/AgCl and or a 0.2%-4% concentration of citric acid. The outer surface can be fitted with a Luer-Lock bearing a two-way valve to permit "loading" of the cathode chamber with deionized water solution containing 0.2%-4.0% concentration of citric acid or another type of buffer solution. In case of hydrogel, the liquid can moisten the surface of the hydrogel and, in case of the mesh, it can fill the air voids of the mesh. For loading, the patch can be applied to the skin. A syringe can be connected. Air can first be aspirated out of the undersurface, fluid can then be injected. Air can again be aspirated out and the fluid can be injected again. This procedure can be similar in mechanics for both positive and negative electrodes.

An insulator bridge can be connected between the electrodes and the patch backing cloth. The insulator bridge can comprise dense foam, having a smooth surface; and an adhesive present on the skin surface. The bridge can separate the two electrodes by 6-8 cm in width. The support material can be, e.g., a hydrophilic foam such as a polyurethane foam, a nonwoven porous polyester, a fibrous or cloth material, etc.

A controller can comprise a rechargeable battery type cleared with market standard and/or the FDA. The controller can comprise a current, voltage monitor and a voltage regulator modulating electron current. (The voltage can be variable between approximately 5 to 50 volts, while the current can remain fixed). The controller can comprise a screen display for time, to set current and have visual clues (red and a green LED/audio alarms. The controller can comprise a large, clearly marked concave control button(s) on the larger surface that is parallel to the skin; the concavity of the button(s) is to enable people with limited grasping ability to use a stick attached to a prosthetic to press the button(s) and to advance the activation tray, thereby activating the patch. A case can be of a pastel color, flat in shape and of a low profile. The controller can comprise a rail connector for patch and charger. The controller can be programmed to allow adjustment of time of dose administration (will permit the dose of drugs to be delivered to the weight of the patient. The controller can further be programmed to emit an audible and/or visual alarm upon completion of treatment. The controller can have an overcurrent cutoff with the ability to store the remaining dose/time of drug administration upon re-power-up. The controller can apply a constant current or pulsed current (depending on the drug to be delivered) at approximately 4 mA by default but changeable through the menu options. The patch's polarity can be fixed at positive for therapy electrode, but can be changeable through menu options, depending on the drug to be delivered. The controller can ramp-up and ramp-down intermittently. The case can be made of durable material and be serviceable to enable the battery to be replaced. The rechargeable battery can be flat and of a standard size and voltage. The pulse width can be controllable by the user in the settings of the graphic user interface of the controller by using buttons, touch screen, remote wireless device, and/or voice command. Pre-sets of optimal settings for several drugs can be stored in the controller. Voice-command option can be initialized upon attachment of the patch to controller. Voice commands can navigate the user through all areas of the graphic program interface of the unit's screen including settings. The unit can be turned off by verbal command in case the user is unable to manually control the system. A first temperature sensor can be connected to the controller and its readings can be used to modulate the heating to maintain a constant temperature over the patch. A second hardwired temperature sensor can be connected via an analog relay to the heater coil power supply to cut power and stop heating in case of excessive temperature. A heater coil can be at the underside of the controller unit and can warm the patch to the optimal temperature to maintain vasodilatation. Optionally, the underside of the patch or the medication solution can contain a mild non-ionic vasodilatory substance such as but not limited to capsaicin to help with the absorption of the medications into the systemic circulation.

The epilator can comprise one cloth strip with sugaring paste applied to it and non-adherent plastic film covering the sugaring adhesive surface. The cloth can have four ink dots on the edges to mark the area of hair epilation on the skin of the user. A medication electrode can be placed within the confines formed by the 4 dots. Instructions of how to use the sugaring strip for hair epilation can be printed on the plastic cover. Use of a sugaring strip can be optional and used to increase delivery of the drugs if their delivery has been inadequate in the past.

A medication container can comprise a water-filled syringe with a blister pouch on a straight-through or t-connector. To dilute the drugs, the user can depress the plunger and break a semi-perforated seal to the lyophilized container with dry medications. In some embodiments, the blister pack or blebs containing dry medications can be contained inside of the syringe, and the mixing could be performed by twisting, depressing, pulling, heating or bending in order to break the seal and allow the components to mix.

As disclosed herein, embodiments enable mixing of a solvent with one or more powdered agents (e.g., lyophilized medication or buffer) prior to iontophoresis delivery. Accordingly, embodiments of the present disclosure enable delivery of medication stored in powdered form. In this way, the medication can have a longer shelf life than conventional gel medications. Moreover, use of the liquid solution and, in some embodiments, the use of a low pressure source, can provide contact with the subject's skin over a known area, thereby preventing burns common with conventional gel medications. Further, embodiments disclosed herein provide various other advantages over conventional iontophoresis methods, including ease of use, measured doses, and all-in-one patches.

Further aspects can provide improved performance over conventional methods. Such aspects include dissolving the medication(s) in water, removing (epilating) hair under the anode, hydrating the skin with soapy water, running iontophoresis for 20, and hydrating the cathode with a buffer (0.5% citric acid) dissolved in solvent.

According to exemplary aspects, the systems and methods disclosed herein can be used for constipation and incontinence, in particular for individuals having a spinal cord injury (SCI). Neostigmine and glycopyrrolate can be used as medications for treating constipation. In one embodiment, neostigmine and glycopyrrolate can be used and the dose delivered can be modulated by the amount of medications applied to the skin and/or the amount of current applied. Delivery via iontophoresis can reduce side effects over intravenous medication while providing similar beneficial effects (bowel movements).

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An iontophoresis system for positioning against skin of a subject, the iontophoresis system comprising: at least one vessel having a solvent therein; an anode apparatus comprising: a first reservoir configured to receive the solvent from the at least one vessel so that, when received into the first reservoir, the solvent makes contact with the skin of the subject; a first electrode positioned above the first reservoir; and a cathode apparatus comprising: a second reservoir configured to receive the solvent from the at least one vessel so that, when received into the first reservoir, the solvent makes contact with the skin of the subject; a second electrode positioned above the second reservoir.

Aspect 2: The iontophoresis system of aspect 1, further comprising a first negative pressure source configured to remove air from the first reservoir.

Aspect 3: The iontophoresis system of aspect 2, further comprising a one-way valve positioned in fluid communication with the first negative pressure source and ambient air, wherein the first negative pressure source comprises a resilient compressible chamber.

Aspect 4: The iontophoresis system of aspect 2 or aspect 3, wherein the first negative pressure source comprises a volume having a negative pressure trapped therein, wherein the iontophoresis system further comprises: a needle configured to pierce the volume having a negative pressure trapped therein, and a conduit that provides fluid communication between the needle and the first reservoir.

Aspect 5: The iontophoresis system of any of aspects 2-4, wherein the first negative pressure source comprises: a syringe chamber, a plunger movable within the syringe chamber, and a check valve configured to allow fluid into the syringe chamber and inhibit fluid from exiting the syringe chamber.

Aspect 6: The iontophoresis system of any of the preceding aspects, further comprising a chamber having a powdered agent disposed therein, wherein the chamber is positioned between, and configured to be in fluid communication with, the first reservoir and the at least one vessel.

Aspect 7: The iontophoresis system of any of the preceding aspects, further comprising a powdered agent disposed in the first reservoir.

Aspect 8: The iontophoresis system of any of the preceding aspects, wherein the at least one vessel comprises a first vessel that is configured to deliver solvent to the first reservoir and a second vessel that is configured to deliver solvent to the second reservoir.

Aspect 9: The iontophoresis system of any of the preceding aspects, further comprising a depolarizer electrode positioned below the first reservoir and positioned to make contact with the skin of the subject.

Aspect 10: The iontophoresis system of any of the preceding aspects, further comprising a controller device comprising: a non-transitory computer readable medium configured to store executable programmed modules; and a processor communicatively coupled with the non-transitory computer readable medium and configured to execute programmed modules stored therein, wherein the controller is configured to control the first electrode to periodically generate a therapeutic electrical pulse having a first charge that creates an electrical voltage difference between the first electrode and the second electrode to transport the charged therapeutic agent through the skin of the subject.

Aspect 11: The iontophoresis system of aspect 10, further comprising a depolarizer electrode positioned below the first reservoir and positioned to make contact with the skin of the subject, wherein the controller is configured to control the depolarizer electrode to periodically generate a depolarizing electrical pulse having a second charge opposite the first charge that creates an electrical voltage difference between the depolarizer electrode and the surface of the skin to depolarize the skin of the subject.

Aspect 12: The iontophoresis system of any of the preceding aspects, further comprising an insulator bridge configured to provide electrical and physical insulation between the first electrode and the second electrode.

Aspect 13: The iontophoresis system of any of the preceding aspects, wherein the at least one vessel comprises a first fluid connector, and the anode apparatus comprises a second fluid connector that is configured to mate with the first fluid connector, wherein the second fluid connector comprises a seal.

Aspect 14: The iontophoresis system of any of aspects 6-13, wherein the powdered agent comprises an ionic surfactant that facilitates the passage of the powdered agent transdermally.

Aspect 15: The iontophoresis system of any of aspects 6-14, wherein the powdered agent comprises citric acid.

Aspect 16: The iontophoresis system of any of aspects 6-15, wherein the powdered agent comprises a di-protic or tri-protic acid.

Aspect 17: The iontophoresis system of any of aspects 6-16, wherein the powdered agent comprises a quantity of acid that, when mixed with the solvent to fill the anode reservoir, provides a concentration of the acid that is non-irritating to the skin.

Aspect 18: The iontophoresis system of aspect 17, wherein the concentration ranges from 0.2% to 2%.

Aspect 19: The iontophoresis system of any of aspects 6-18, wherein an acid solution resulting from mixing the powdered agent and solvent provides buffering to the electrochemical generation of a base.

Aspect 20: The iontophoresis system of aspect 19, wherein the base is hydroxide ions.

Aspect 21: A method for iontophoresis comprising: securing an anode apparatus to the skin of the subject, the anode apparatus having a first reservoir configured to receive solvent so that, when received into the first reservoir, the solvent makes contact with the skin of the subject, and a first electrode positioned above the first reservoir; securing a cathode apparatus to the skin of the subject, the cathode apparatus having a second reservoir configured to receive the solvent so that, when received into the first reservoir, the solvent makes contact with the skin of the subject, and a second electrode positioned above the second reservoir; discharging a solvent from at least one vessel to mix with a first powdered agent and enter the anode apparatus; discharging the solvent from the at least one vessel to mix with a second powdered agent and enter the cathode apparatus; and generating a therapeutic direct electrical pulse having a first charge that creates an electrical voltage difference between the first electrode and the second electrode to transport the charged therapeutic agent through the skin of the subject.

Aspect 22: The method of aspect 21, further comprising generating a depolarizing electrical pulse by a depolarizing electrode in contact with the skin, the depolarizing electrical pulse having an electric charge opposite of an electric charge on the surface of the skin to depolarize the skin of the subject.

Aspect 23: The method of aspect 21 or aspect 22, wherein the hair of the subject in the first position on the skin is epilated prior to securing the anode apparatus to the epilated area of the skin of the subject.

Aspect 24: The method of aspect 23, wherein the hair of the subject is epilated by sugaring.

Aspect 25: The method of aspect 24, further comprising epilating the skin by sugaring.

Aspect 26: The method of any of aspects 21-25, wherein the first powdered agent is one of neostigmine, glycopyrrolate, fentanyl, alendronate, insulin, citric acid, lidocaine, vitamin B12, sumatriptan, or any other ionizable therapeutic substance.

Aspect 27: The method of aspect any of aspects 21-26, wherein a duration of the therapeutic electrical pulse is determined at least in part by settings of a controller device in communication with the first electrode and the second electrode.

Although the foregoing invention has been described in some detail by way of illustration and example for purposes of clarity of understanding, certain changes and modifications may be practiced within the scope of the appended claims.

What is claimed is:

1. An iontophoresis system for positioning against skin of a subject, the iontophoresis system comprising:
   at least one vessel having a solvent therein;
   an anode apparatus comprising:
      a first reservoir configured to receive the solvent from the at least one vessel so that, when received into the first reservoir, the solvent makes contact with the skin of the subject;
      a first electrode positioned above the first reservoir;
   a cathode apparatus comprising:
      a second reservoir configured to receive the solvent from the at least one vessel so that, when received into the second reservoir, the solvent makes contact with the skin of the subject;
      a second electrode positioned above the second reservoir;
      a first conduit that extends between and is in communication with the at least one vessel and the first reservoir, wherein the first conduit is configured to permit communication of solvent between the at least one vessel and the first reservoir; and
      a second conduit that extends between and is in communication with the at least one vessel and the second reservoir, wherein the second conduit is configured to permit communication of solvent between the at least one vessel and the second reservoir,
      wherein the first conduit and the first reservoir cooperate to define a first solvent delivery pathway,
      wherein the iontophoresis system further comprises at least one powdered agent disposed within the first solvent delivery pathway so that delivery of the solvent to the first reservoir causes mixing with the at least one powdered agent to form a solution.

2. The iontophoresis system of claim 1, further comprising a first negative pressure source configured to remove air from the first reservoir.

3. The iontophoresis system of claim 2, further comprising a one-way valve positioned in fluid communication with the first negative pressure source and ambient air, wherein the first negative pressure source comprises a resilient compressible chamber.

4. The iontophoresis system of claim 2, wherein the first negative pressure source comprises a volume having a negative pressure trapped therein, wherein the iontophoresis system further comprises:
   a needle configured to pierce the volume having a negative pressure trapped therein, and
   a third conduit that provides fluid communication between the needle and the first reservoir.

5. The iontophoresis system of claim 2, wherein the first negative pressure source comprises:
   a syringe chamber,
   a plunger movable within the syringe chamber, and
   a check valve configured to allow fluid into the syringe chamber and inhibit fluid from exiting the syringe chamber.

6. The iontophoresis system of claim 1, wherein the first conduit comprises a chamber having the at least one powdered agent disposed therein, wherein the chamber is positioned between, and configured to be in fluid communication with, the first reservoir and the at least one vessel.

7. The iontophoresis system of claim 1, wherein the at least one powdered agent is disposed in the first reservoir.

8. The iontophoresis system of claim 1, wherein the at least one vessel comprises a first vessel that is configured to deliver solvent to the first reservoir and a second vessel that is configured to deliver solvent to the second reservoir.

9. The iontophoresis system of claim 1, further comprising a depolarizer electrode positioned below the first reservoir and positioned to make contact with the skin of the subject.

10. The iontophoresis system of claim 1, further comprising a controller device comprising:
    a non-transitory computer readable medium configured to store executable programmed modules; and
    a processor communicatively coupled with the non-transitory computer readable medium and configured to execute programmed modules stored therein;
    wherein the controller is configured to control the first electrode to periodically generate a therapeutic electrical pulse having a first charge that creates an electrical voltage difference between the first electrode and the second electrode to transport the charged therapeutic agent through the skin of the subject.

11. The iontophoresis system of claim 10, further comprising a depolarizer electrode positioned below the first reservoir and positioned to make contact with the skin of the subject, wherein the controller is configured to control the depolarizer electrode to periodically generate a depolarizing electrical pulse having a second charge opposite the first charge that creates an electrical voltage difference between the depolarizer electrode and the surface of the skin to depolarize the skin of the subject.

12. The iontophoresis system of claim 1, further comprising an insulator bridge configured to provide electrical and physical insulation between the first electrode and the second electrode.

13. The iontophoresis system of claim 1, wherein the at least one vessel comprises a first fluid connector, and the anode apparatus comprises a second fluid connector that is configured to mate with the first fluid connector, wherein the second fluid connector comprises a seal.

14. The iontophoresis system of claim 6, wherein the at least one powdered agent comprises an ionic surfactant that facilitates the passage of the at least one powdered agent transdermally.

15. The iontophoresis system of claim 1, wherein the second conduit and the second reservoir cooperate to define a second solvent delivery pathway, wherein the iontophoresis system further comprises at least one additional powdered agent disposed within the second solvent delivery pathway so that delivery of the solvent to the second reservoir causes mixing with the at least one powdered agent to form a second solution, wherein the at least one additional powdered agent comprises citric acid.

16. The iontophoresis system of claim 1, wherein the second conduit and the second reservoir cooperate to define a second solvent delivery pathway, wherein the iontophoresis system further comprises at least one additional powdered agent disposed within the second solvent delivery pathway disposed so that delivery of the solvent to the second reservoir causes mixing with the at least one powdered agent to form a second solution, wherein the at least one additional powdered agent comprises a di-protic or tri-protic acid.

17. The iontophoresis system of claim 6, wherein the at least one powdered agent comprises a quantity of acid that, when mixed with the solvent to fill the anode reservoir, provides a concentration of the acid that is non-irritating to the skin.

18. The iontophoresis system of claim 17, wherein the concentration ranges from 0.2% to 2%.

19. The iontophoresis system of claim 1, further comprising an acid in the second reservoir that provides buffering to the electrochemical generation of a base.

20. The iontophoresis system of claim 19, wherein the base is hydroxide ions.

21. The iontophoresis system of claim 1, further comprising a vertical spacer disposed within the first reservoir.

22. The iontophoresis system of claim 1, wherein the iontophoresis system is wireless.

* * * * *